(12) United States Patent
Ishikawa et al.

(10) Patent No.: US 10,190,107 B2
(45) Date of Patent: Jan. 29, 2019

(54) MODIFIED β-GALACTOSIDASE

(71) Applicant: Amano Enzyme Inc., Nagoya-shi (JP)

(72) Inventors: Kazuhiko Ishikawa, Ikeda (JP); Satoru Ishihara, Kakamigahara (JP); Shotaro Yamaguchi, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 0 days.

(21) Appl. No.: 15/503,162

(22) PCT Filed: Aug. 13, 2015

(86) PCT No.: PCT/JP2015/072885
§ 371 (c)(1),
(2) Date: Feb. 10, 2017

(87) PCT Pub. No.: WO2016/027747
PCT Pub. Date: Feb. 25, 2016

(65) Prior Publication Data
US 2017/0233705 A1    Aug. 17, 2017

(30) Foreign Application Priority Data
Aug. 19, 2014    (JP) .................................. 2014-166897

(51) Int. Cl.
| | | |
|---|---|---|
| *C12N 9/24* | (2006.01) | |
| *C12N 1/00* | (2006.01) | |
| *C12N 15/09* | (2006.01) | |
| *C12P 19/04* | (2006.01) | |
| *C12P 19/14* | (2006.01) | |

(52) U.S. Cl.
CPC ............. *C12N 9/2402* (2013.01); *C12N 1/00* (2013.01); *C12N 15/09* (2013.01); *C12P 19/04* (2013.01); *C12P 19/14* (2013.01); *C12Y 302/01023* (2013.01)

(58) Field of Classification Search
None
See application file for complete search history.

(56) References Cited

U.S. PATENT DOCUMENTS 9,516,888 B2 * 12/2016 Katase ................. A23C 9/1206
2012/0135468 A1    5/2012 Katase et al.
(Continued)

FOREIGN PATENT DOCUMENTS

WO       2010/140435 A1   12/2010

OTHER PUBLICATIONS

Supplementary European Search Report dated Nov. 27, 2017, issued for the European patent application No. 15834600.
(Continued)

*Primary Examiner* — Richard C Ekstrom
(74) *Attorney, Agent, or Firm* — Locke Lord LLP

(57) ABSTRACT

The present invention has a purpose of providing a technique for increasing the heat resistance of a β-galactosidase. According to the present invention, in a reference β-galactosidase amino acid sequence which shows a 90% or more identity to the amino acid sequence of SEQ ID NO: 4, proline is substituted for one or more amino acids selected from the group consisting of the following amino acids: (1) an amino acid corresponding to lysine at position 166 of the amino acid sequence of SEQ ID NO: 4, (2) an amino acid corresponding to glycine at position 307 of the amino acid sequence of SEQ ID NO: 4, and (3) an amino acid corresponding to alanine at position 833 of the amino acid sequence of SEQ ID NO: 4.

14 Claims, 4 Drawing Sheets
Specification includes a Sequence Listing.

(A) Activities measured at 40°C and 60°C

| Sample | 40°C (U/ml) | 60°C (U/ml) |
|---|---|---|
| WT | 206.6 | 218.4 |
| G101P_G102P | 83.9 | 0.114 |
| K166P | 210.1 | 205.2 |
| D167P | 165.1 | 168.9 |
| G306P | 49.2 | 55.4 |
| G307P | 126.8 | 132.9 |
| G349P | 163.9 | 0 |
| E720P | 210.5 | 230.8 |
| A833P | 211.1 | 195.2 |
| T211C_T315C | 107.9 | 125.8 |

(B) Relative activity ratio

(56) References Cited

U.S. PATENT DOCUMENTS

| | | | |
|---|---|---|---|
| 2016/0251689 A1* | 9/2016 | Nakamura | C12Y 302/01023 435/99 |
| 2017/0049120 A1* | 2/2017 | Katase | A23C 9/1206 |
| 2017/0198271 A1* | 7/2017 | Choi | C12N 9/2471 |
| 2017/0233705 A1* | 8/2017 | Ishikawa | C12N 9/2402 435/99 |

OTHER PUBLICATIONS

J. Song et al. "Causes of the Production of Multiple Forms of beta-Galactosidase by Bacillus circulans," Bioscience, Biotechnology, and Biochemistry, 2011, 75(2), pp. 268-278. (discussed in the spec).

J. Song et al. "Cloning and Expression of a beta-Galactosidase Gene of Bacillus circulans," Bioscience, Biotechnology, and Biochemistry, 2011, 75(6), pp. 1194-1197. (cited in the ISR).

R. A. Edwards et al. "Thermal Denaturation of beta-Galactosulase and of Two Site-Specific Mutants," Biochemisry, 1990, 29, pp. 11001-11008. (cited in the ISR).

J. Song et al. "The Discoidin Domain of Bacillus circulans beta-Galactosulase Plays an Essential Role in Repressing Galactooligosaccharide Production," Bioscience, Biotechnology, and Biochemistry, 2013, 77(1), pp. 73-79. (cited in the ISR).

K. Ishikawa et al. "Crystal structure of beta-galactosidase from Bacillus circulans ATCC 31382(BgaD) and the construction of the thermophilic mutants," FEBS Journal, 2015, 282, pp. 2540-2552.

International Search Report dated Nov. 17, 2015, issued for PCT/JP2015/072885.

* cited by examiner (A) Activities measured at 40°C and 60°C

| Sample | 40°C (U/ml) | 60°C (U/ml) |
|---|---|---|
| WT | 206.6 | 218.4 |
| G101P_G102P | 83.9 | 0.114 |
| K166P | 210.1 | 205.2 |
| D167P | 165.1 | 168.9 |
| G306P | 49.2 | 55.4 |
| G307P | 126.8 | 132.9 |
| G349P | 163.9 | 0 |
| E720P | 210.5 | 230.8 |
| A833P | 211.1 | 195.2 |
| T211C_T315C | 107.9 | 125.8 |

(B) Relative activity ratio

|  | Tm (°C) |
|---|---|
| WT | 72.5±0.49 |
| K166P | 75.4±0.22 |
| D167P | 72.4±0.32 |
| G254P | 72.5±0.30 |
| G307P | 72.8±0.19 |
| E720P | 69.4±0.27 |
| A833P | 72.9±0.19 |
| T211C/T315C | 72.7±0.24 |

*FIG.2*

|                     | Tm (°C)     |
|---------------------|-------------|
| WT                  | 72.5±0.49   |
| K166P_G307P         | 75.8±0.21   |
| K166P_A833P         | 74.3±0.16   |
| G307P_A833P         | 73.4±0.18   |
| K166P_G307P_A833P   | 76.7±0.22   |

FIG.3

SEQUENCE LISTING

<160> NUMBER OF SEQ ID NOS: 15

<210> SEQ ID NO 1
<211> LENGTH: 1737
<212> TYPE: PRT
<213> ORGANISM: Bacillus circulans

<400> SEQUENCE: 1

```
Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
        50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Gly Ile Gly Trp Tyr Arg
            100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Glu Lys Thr Ala Ala Ala Gly
            260                 265                 270

Thr Val Thr Pro Phe Glu Gln Asn Thr Val Ile Lys Gln Pro Lys Leu
        275                 280                 285
```

```
Trp Ser Ile Asp Lys Pro Tyr Arg Tyr Asn Leu Val Thr Glu Val Ile
290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
                340                 345                 350

Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
                420                 425                 430

Gly Lys Asn Glu Pro Ala Ile Ile Met Trp Ser Ile Gly Asn Glu Ile
            435                 440                 445

Tyr Asp Thr Thr Asn Ala Ala Gly Val Glu Thr Ala Arg Asn Leu Val
450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
                500                 505                 510

Glu Asn Asn Tyr Asp Gly Tyr His Lys Gln Asn Pro Ser Trp Lys Leu
            515                 520                 525

Tyr Gly Ser Glu Thr Ser Ser Ala Thr Arg Ser Arg Gly Val Tyr Thr
530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
                580                 585                 590

Trp Thr Gly Phe Asp Tyr Ile Gly Glu Pro Thr Pro Tyr Tyr Asn Ser
            595                 600                 605

Tyr Pro Ala Lys Ser Ser Tyr Phe Gly Ala Val Asp Thr Ala Gly Phe
610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
                660                 665                 670

Gly Glu Ser Leu Gly Glu Lys Asn Tyr Asp Asn Lys Gln Thr Ser Trp
            675                 680                 685

Gly Ala Pro Tyr Lys Glu Thr Lys Asp Gly Lys Thr Tyr Leu Glu Trp
690                 695                 700
```

-continued

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
            725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
            755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
                820                 825                 830

Ala Gly Leu Ser Ser Asp Ser Thr Ser Val Phe Thr Val Thr Pro Ala
            835                 840                 845

Asp His Asp Lys Lys Ile Val Ala Gly Ile Asp Asp Val Asn Leu Thr
850                 855                 860

Val Asp Val Asn Glu Ala Pro Lys Leu Pro Ser Glu Ile Lys Val Tyr
865                 870                 875                 880

Tyr Ser Asp Glu Ser Ala Ala Ala Lys Asn Val Thr Trp Asp Glu Val
                885                 890                 895

Asp Pro Lys Gln Tyr Ser Thr Val Gly Glu Phe Thr Val Glu Gly Ser
            900                 905                 910

Val Glu Gly Thr Ser Leu Lys Ala Lys Ala Phe Val Ile Val Lys Gly
            915                 920                 925

Ile Val Ala Val Lys Pro Tyr Ser Thr Ala Thr Lys Val Gly Val Gln
    930                 935                 940

Pro Val Leu Pro Glu Lys Ala Thr Leu Leu Tyr Ser Asp Gly Thr Thr
945                 950                 955                 960

Lys Gly Ala Thr Val Thr Trp Asp Glu Ile Pro Glu Asp Lys Leu Ala
            965                 970                 975

Lys Glu Gly Arg Phe Thr Val Glu Gly Ser Val Glu Gly Thr Asp Leu
            980                 985                 990

Lys Ala Asn Val Tyr Val Arg Val Thr Asn Glu Val Lys Ser Val Asn
            995                 1000                1005

Ile Met Leu Gln Glu Gln Gly Ser Ala Tyr Pro Lys Leu Glu Ala
    1010                1015                1020

Thr Phe Thr Asn Pro Ala Asp Asn Leu Gln His Leu Asn Asp Gly
    1025                1030                1035

Ile Lys Ser Tyr Thr Asn Asn Pro Val Asn Arg Trp Thr Asn Trp
    1040                1045                1050

Thr Arg Thr Pro Arg Asp Ala Gly Asp Ser Ile Thr Val Asn Phe
    1055                1060                1065

Gly Lys Lys His Val Ile Asn Asn Leu Asp Leu Phe Val Phe Thr
    1070                1075                1080

Asp Ser Gly Thr Val Val Pro Glu Lys Ala Glu Val Gln Tyr Trp
    1085                1090                1095

Asp Gly Thr Ala Trp Lys Val Glu Asn Leu Thr Gln Pro Ser
    1100                1105                1110

Pro Tyr Val Val Glu Lys Asn Glu Leu Thr Phe Asp Ala Val Ala

-continued

```
            1115                1120                1125
Thr Glu Lys Leu Lys Phe His Leu Thr Pro Ser Val Lys Gly Lys
            1130                1135                1140
Phe Leu Ala Leu Thr Glu Ala Glu Val Tyr Ala Asp Gln Ile Val
            1145                1150                1155
Met Gly Glu Thr Ala Lys Leu Gln Ser Ile Thr Val Asn Gly Lys
            1160                1165                1170
Ala Leu Glu Gly Phe Asp His Ala Lys Lys Asn Tyr Glu Leu Val
            1175                1180                1185
Leu Pro Tyr Gly Ser Glu Leu Pro Lys Ile Glu Ala Ala Ala Ala
            1190                1195                1200
Asp Asn Ala Thr Val Thr Ile Leu Pro Ala Phe Ser Tyr Pro Gly
            1205                1210                1215
Thr Ala Lys Leu Phe Val Thr Ser Glu Asp Gly Lys Val Thr Thr
            1220                1225                1230
Glu Tyr Ser Ile Gly Val Ser Thr Glu Glu Pro Lys Leu Val Ser
            1235                1240                1245
Ala Glu Leu Ser Ala Asp Lys Thr Asn Val Met Glu Asp Asp Ile
            1250                1255                1260
Ile Asp Leu Lys Val Ile Gly Leu Phe Glu Ser Lys Glu Lys Ile
            1265                1270                1275
Asp Val Thr Asp Ser Gln Pro Thr Tyr Glu Phe Asp Gln Gln Ile
            1280                1285                1290
Ile Lys Ile Glu Gly Asn Lys Leu Tyr Ala Leu Glu Thr Gly Asn
            1295                1300                1305
Val Lys Val Lys Val Thr Val Thr Tyr Lys Gly Val Ser Val Thr
            1310                1315                1320
Thr Pro Ala Leu Glu Phe Thr Ile Ala Lys Asn Pro Ala Pro Lys
            1325                1330                1335
Tyr Ile Thr Ser Leu Glu Pro Val Thr Val Val Lys Lys Gly
            1340                1345                1350
Glu Ala Pro Glu Leu Pro Ala Thr Val Val Ala His Tyr Asn Arg
            1355                1360                1365
Gly Ile Pro Arg Asp Val Lys Val Lys Trp Glu Arg Ile Asn Pro
            1370                1375                1380
Ser Lys Tyr Gln Gln Leu Gly Glu Phe Thr Val Ser Gly Met Val
            1385                1390                1395
Glu Gly Thr Asp Ile Lys Ala Gln Ala Lys Val Ile Val Lys Gly
            1400                1405                1410
Ala Val Ala Val Glu Asp Ile Arg Met Ala Val Leu Leu Lys Gln
            1415                1420                1425
Met Pro Gln Leu Pro Gly Lys Val Thr Val Tyr Tyr Ser Asp Gly
            1430                1435                1440
Ala Glu Glu Gln Arg Ala Val Lys Trp Glu Glu Ile Pro Gln Glu
            1445                1450                1455
Glu Leu Glu Asn Val Gly Glu Phe Lys Val Lys Gly Asp Val Asn
            1460                1465                1470
Gly Val Lys Leu Lys Ala Thr Ala Thr Ile Arg Val Thr Asp Glu
            1475                1480                1485
Val Gly Gly Glu Gln Asn Ile Ser Arg Ala Lys Asn Gly Tyr Glu
            1490                1495                1500
Tyr Pro Lys Ala Glu Ala Ser Phe Thr Asn Asn Gly Pro Gly Ser
            1505                1510                1515
```

```
Ser Asp Arg Ile Glu Ala Ile Asn Asp Asp Val Ile Ser Tyr Glu
    1520                1525                1530

Ala Asn Pro His Asn Arg Trp Thr Asn Trp Gln Pro Val Pro Arg
    1535                1540                1545

Ala Gly Asp Trp Val Ser Ile Thr Phe Gly Asp Tyr Glu Pro Thr
    1550                1555                1560

Glu Tyr Asp Val Asp Ser Met Glu Ile His Trp Phe Ala Asp His
    1565                1570                1575

Gly Thr Ser Tyr Pro Glu Arg Phe Gln Ile Glu Tyr Lys Ser Gly
    1580                1585                1590

Asp Ser Trp Lys Glu Val Thr Ser Leu Lys Ser Asp Pro Ala Ser
    1595                1600                1605

Pro Ala Leu Gly Lys Ala Asn Val Tyr Ser Phe Asp Arg Val Lys
    1610                1615                1620

Thr Ser Ala Ile Arg Val Lys Met Thr Ala Gln Ala Gly Lys Ser
    1625                1630                1635

Leu Ala Ile Thr Glu Leu Lys Val Phe Ser Lys Trp Pro Lys Ala
    1640                1645                1650

Gly Thr Glu Pro Glu Val Thr Asp Ile Lys Val Gly Gly Lys Ser
    1655                1660                1665

Ile Leu Glu Asp Phe Glu Gln Lys Gly Asp His Tyr Glu Val Thr
    1670                1675                1680

Ile Asp Ala Gly Asp Ala Asn Val Met Pro Lys Ile Asn Val Lys
    1685                1690                1695

Ala Lys Asp Gln Thr Ser Ile Thr Ile Val Pro Ala Val Thr Ser
    1700                1705                1710

Pro Ser Thr Ala Lys Val Ile Ala Lys Ser Glu Asp Gly Lys Lys
    1715                1720                1725

Val Lys Val Tyr Ser Ile His Tyr Lys
    1730                1735

<210> SEQ ID NO 2
<211> LENGTH: 1422
<212> TYPE: PRT
<213> ORGANISM: Bacillus circulans

<400> SEQUENCE: 2

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
        50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Gly Ile Gly Trp Tyr Arg
                100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
```

```
              130                 135                 140
Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
                180                 185                 190

Tyr Arg Asn Val Tyr Leu Thr Val Thr Asp Pro Ile His Val Ala Arg
                195                 200                 205

Tyr Gly Thr Phe Val Thr Thr Pro Asn Leu Glu Lys Ser Ile Lys Glu
                210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
                260                 265                 270

Thr Val Thr Pro Phe Glu Gln Asn Thr Val Ile Lys Gln Pro Lys Leu
                275                 280                 285

Trp Ser Ile Asp Lys Pro Tyr Arg Tyr Asn Leu Val Thr Glu Val Ile
                290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
                340                 345                 350

Ala Ala Thr Asn Ala Arg Gly Val Glu Arg Gln Met Gln Ile Met Lys
                355                 360                 365

Asp Met Gly Val Asn Ala Ile Arg Val Thr His Asn Pro Ala Ser Pro
370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
                420                 425                 430

Gly Lys Asn Glu Pro Ala Ile Ile Met Trp Ser Ile Gly Asn Glu Ile
                435                 440                 445

Tyr Asp Thr Thr Asn Ala Ala Gly Val Glu Thr Ala Arg Asn Leu Val
                450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
                500                 505                 510

Glu Asn Asn Tyr Asp Gly Tyr His Lys Gln Asn Pro Ser Trp Lys Leu
                515                 520                 525

Tyr Gly Ser Glu Thr Ser Ser Ala Thr Arg Ser Arg Gly Val Tyr Thr
                530                 535                 540

His Pro Tyr Gln Tyr Asn Gln Ser Thr Lys Tyr Ala Asp Leu Gln Gln
545                 550                 555                 560
```

```
Ser Ser Tyr Asp Asn Asp Tyr Val Gly Trp Gly Arg Thr Ala Glu Asp
            565                 570                 575

Ala Trp Lys Tyr Asp Arg Asp Leu Lys His Ile Ala Gly Gln Phe Ile
        580                 585                 590

Trp Thr Gly Phe Asp Tyr Ile Gly Glu Pro Thr Pro Tyr Tyr Asn Ser
    595                 600                 605

Tyr Pro Ala Lys Ser Ser Tyr Phe Gly Ala Val Asp Thr Ala Gly Phe
610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
            820                 825                 830

Ala Gly Leu Ser Ser Asp Ser Thr Ser Val Phe Thr Val Thr Pro Ala
        835                 840                 845

Asp His Asp Lys Lys Ile Val Ala Gly Ile Asp Asp Val Asn Leu Thr
    850                 855                 860

Val Asp Val Asn Glu Ala Pro Lys Leu Pro Ser Glu Ile Lys Val Tyr
865                 870                 875                 880

Tyr Ser Asp Glu Ser Ala Ala Lys Asn Val Thr Trp Asp Glu Val
                885                 890                 895

Asp Pro Lys Gln Tyr Ser Thr Val Gly Glu Phe Thr Val Glu Gly Ser
            900                 905                 910

Val Glu Gly Thr Ser Leu Lys Ala Lys Ala Phe Val Ile Val Lys Gly
        915                 920                 925

Ile Val Ala Val Lys Pro Tyr Ser Thr Ala Thr Lys Val Gly Val Gln
    930                 935                 940

Pro Val Leu Pro Glu Lys Ala Thr Leu Leu Tyr Ser Asp Gly Thr Thr
945                 950                 955                 960

Lys Gly Ala Thr Val Thr Trp Asp Glu Ile Pro Glu Asp Lys Leu Ala
                965                 970                 975
```

-continued

```
Lys Glu Gly Arg Phe Thr Val Glu Gly Ser Val Glu Gly Thr Asp Leu
            980                 985                 990

Lys Ala Asn Val Tyr Val Arg Val  Thr Asn Glu Val Lys  Ser Val Asn
        995                 1000                1005

Ile Met Leu Gln Glu Gln Gly  Ser Ala Tyr Pro Lys  Leu Glu Ala
        1010                1015                1020

Thr Phe Thr Asn Pro Ala Asp  Asn Leu Gln His Leu  Asn Asp Gly
        1025                1030                1035

Ile Lys Ser Tyr Thr Asn Asn  Pro Val Asn Arg Trp  Thr Asn Trp
        1040                1045                1050

Thr Arg Thr Pro Arg Asp Ala  Gly Asp Ser Ile Thr  Val Asn Phe
        1055                1060                1065

Gly Lys Lys His Val Ile Asn  Asn Leu Asp Leu Phe  Val Phe Thr
        1070                1075                1080

Asp Ser Gly Thr Val Val Pro  Glu Lys Ala Glu Val  Gln Tyr Trp
        1085                1090                1095

Asp Gly Thr Ala Trp Lys Asp  Val Glu Asn Leu Thr  Gln Pro Ser
        1100                1105                1110

Pro Tyr Val Val Glu Lys Asn  Glu Leu Thr Phe Asp  Ala Val Ala
        1115                1120                1125

Thr Glu Lys Leu Lys Phe His  Leu Thr Pro Ser Val  Lys Gly Lys
        1130                1135                1140

Phe Leu Ala Leu Thr Glu Ala  Glu Val Tyr Ala Asp  Gln Ile Val
        1145                1150                1155

Met Gly Glu Thr Ala Lys Leu  Gln Ser Ile Thr Val  Asn Gly Lys
        1160                1165                1170

Ala Leu Glu Gly Phe Asp His  Ala Lys Lys Asn Tyr  Glu Leu Val
        1175                1180                1185

Leu Pro Tyr Gly Ser Glu Leu  Pro Lys Ile Glu Ala  Ala Ala Ala
        1190                1195                1200

Asp Asn Ala Thr Val Thr Ile  Leu Pro Ala Phe Ser  Tyr Pro Gly
        1205                1210                1215

Thr Ala Lys Leu Phe Val Thr  Ser Glu Asp Gly Lys  Val Thr Thr
        1220                1225                1230

Glu Tyr Ser Ile Gly Val Ser  Thr Glu Glu Pro Lys  Leu Val Ser
        1235                1240                1245

Ala Glu Leu Ser Ala Asp Lys  Thr Asn Val Met Glu  Asp Asp Ile
        1250                1255                1260

Ile Asp Leu Lys Val Ile Gly  Leu Phe Glu Ser Lys  Glu Lys Ile
        1265                1270                1275

Asp Val Thr Asp Ser Gln Pro  Thr Tyr Glu Phe Asp  Gln Gln Ile
        1280                1285                1290

Ile Lys Ile Glu Gly Asn Lys  Leu Tyr Ala Leu Glu  Thr Gly Asn
        1295                1300                1305

Val Lys Val Lys Val Thr Val  Thr Tyr Lys Gly Val  Ser Val Thr
        1310                1315                1320

Thr Pro Ala Leu Glu Phe Thr  Ile Ala Lys Asn Pro  Ala Pro Lys
        1325                1330                1335

Tyr Ile Thr Ser Leu Glu Pro  Val Thr Val Val Val  Lys Lys Gly
        1340                1345                1350

Glu Ala Pro Glu Leu Pro Ala  Thr Val Val Ala His  Tyr Asn Arg
        1355                1360                1365

Gly Ile Pro Arg Asp Val Lys  Val Lys Trp Glu Arg  Ile Asn Pro
```

-continued

```
             1370                1375                1380
Ser  Lys  Tyr  Gln  Gln  Leu  Gly  Glu  Phe  Thr  Val  Ser  Gly  Met  Val
     1385                1390                1395

Glu  Gly  Thr  Asp  Ile  Lys  Ala  Gln  Ala  Lys  Val  Ile  Val  Lys  Gly
     1400                1405                1410

Ala  Val  Ala  Val  Glu  Asp  Ile  Arg  Met
     1415                1420

<210> SEQ ID NO 3
<211> LENGTH: 1249
<212> TYPE: PRT
<213> ORGANISM: Bacillus circulans

<400> SEQUENCE: 3

Met  Lys  Lys  Ala  Ile  Ser  Cys  Val  Phe  Leu  Ile  Ser  Ala  Leu  Ile  Leu
1                  5                   10                  15

Ser  Ser  Phe  Gln  Val  Pro  Val  Gln  Gly  Gln  Ala  Met  Ser  Lys  Thr  Thr
                 20                  25                  30

Ser  Ala  Ala  Gly  Asn  Ser  Val  Ser  Tyr  Asp  Gly  Glu  Arg  Arg  Val  Asn
             35                  40                  45

Phe  Asn  Glu  Asn  Trp  Arg  Phe  Gln  Arg  Glu  Thr  Asn  Gly  Ser  Ile  Ala
     50                  55                  60

Gly  Ala  Gln  Asn  Pro  Gly  Phe  Asp  Asp  Ser  Ser  Trp  Arg  Lys  Leu  Asn
65                   70                  75                  80

Leu  Pro  His  Asp  Trp  Ser  Ile  Glu  Leu  Asp  Phe  Asn  Lys  Asn  Ser  Leu
                     85                  90                  95

Ala  Thr  His  Glu  Gly  Gly  Tyr  Leu  Asp  Gly  Ile  Gly  Trp  Tyr  Arg
                 100                 105                 110

Lys  Thr  Phe  Thr  Ile  Pro  Glu  Ser  Met  Lys  Gly  Lys  Arg  Ile  Ser  Leu
             115                 120                 125

Asp  Phe  Asp  Gly  Val  Tyr  Met  Asn  Ser  Thr  Thr  Tyr  Leu  Asn  Gly  Glu
     130                 135                 140

Val  Leu  Gly  Thr  Tyr  Pro  Phe  Gly  Tyr  Asn  Ala  Phe  Ser  Tyr  Asp  Ile
145                  150                 155                 160

Ser  Asp  Lys  Leu  Tyr  Lys  Asp  Gly  Arg  Ala  Asn  Val  Leu  Val  Val  Lys
                 165                 170                 175

Val  Asn  Asn  Thr  Gln  Pro  Ser  Ser  Arg  Trp  Tyr  Ser  Gly  Ser  Gly  Ile
             180                 185                 190

Tyr  Arg  Asn  Val  Tyr  Leu  Thr  Val  Thr  Asp  Pro  Ile  His  Val  Ala  Arg
     195                 200                 205

Tyr  Gly  Thr  Phe  Val  Thr  Thr  Pro  Asn  Leu  Glu  Lys  Ser  Ile  Lys  Glu
         210                 215                 220

Asp  Arg  Ala  Asp  Val  Asn  Ile  Lys  Thr  Lys  Ile  Ser  Asn  Asp  Ala  Ala
225                  230                 235                 240

Glu  Ala  Lys  Gln  Val  Lys  Ile  Lys  Ser  Thr  Ile  Tyr  Asp  Gly  Ala  Gly
                 245                 250                 255

Asn  Thr  Val  Gln  Thr  Val  Glu  Thr  Glu  Lys  Thr  Ala  Ala  Ala  Gly
             260                 265                 270

Thr  Val  Thr  Pro  Phe  Glu  Gln  Asn  Thr  Val  Ile  Lys  Gln  Pro  Lys  Leu
     275                 280                 285

Trp  Ser  Ile  Asp  Lys  Pro  Tyr  Arg  Tyr  Asn  Leu  Val  Thr  Glu  Val  Ile
     290                 295                 300

Val  Gly  Gly  Gln  Thr  Val  Asp  Thr  Tyr  Glu  Thr  Lys  Phe  Gly  Val  Arg
305                  310                 315                 320
```

```
Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
    450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
            645                 650                 655

Arg Val Leu Ala Tyr Thr Asn Ala Ser Lys Val Glu Leu Val Leu Asn
        660                 665                 670

Gly Glu Ser Leu Gly Glu Lys Asn Tyr Asp Lys Gln Thr Ser Trp
    675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Val Ala Lys Asp Glu
705                 710                 715                 720

Asn Gly Lys Val Ile Ala Arg Asp Gln Val Val Thr Ala Gly Glu Pro
            725                 730                 735

Ala Ser Val Arg Leu Thr Ala Asp Arg Lys Val Val Lys Ala Asp Gly
```

```
                    740             745             750
Thr Asp Leu Ser Phe Ile Thr Ala Asp Ile Val Asp Ser Lys Gly Ile
                755             760             765
Val Val Pro Asp Ala Asp His Leu Ile Thr Phe Asn Val Thr Gly Gln
                770             775             780
Gly Glu Leu Ala Gly Val Asp Asn Gly Asn Ala Ser Ser Val Glu Arg
785             790             795             800
Tyr Lys Asp Asn Lys Arg Lys Ala Phe Ser Gly Lys Ala Leu Ala Ile
                805             810             815
Val Gln Ser Ser Lys Leu Ser Gly Lys Ile Thr Val His Ala Ser Val
                820             825             830
Ala Gly Leu Ser Ser Asp Ser Thr Ser Val Phe Thr Val Thr Pro Ala
                835             840             845
Asp His Asp Lys Lys Ile Val Ala Gly Ile Asp Asp Val Asn Leu Thr
                850             855             860
Val Asp Val Asn Glu Ala Pro Lys Leu Pro Ser Glu Ile Lys Val Tyr
865             870             875             880
Tyr Ser Asp Glu Ser Ala Ala Ala Lys Asn Val Thr Trp Asp Glu Val
                885             890             895
Asp Pro Lys Gln Tyr Ser Thr Val Gly Glu Phe Thr Val Glu Gly Ser
                900             905             910
Val Glu Gly Thr Ser Leu Lys Ala Lys Ala Phe Val Ile Val Lys Gly
                915             920             925
Ile Val Ala Val Lys Pro Tyr Ser Thr Ala Thr Lys Val Gly Val Gln
                930             935             940
Pro Val Leu Pro Glu Lys Ala Thr Leu Leu Tyr Ser Asp Gly Thr Thr
945             950             955             960
Lys Gly Ala Thr Val Thr Trp Asp Glu Ile Pro Glu Asp Lys Leu Ala
                965             970             975
Lys Glu Gly Arg Phe Thr Val Glu Gly Ser Val Glu Gly Thr Asp Leu
                980             985             990
Lys Ala Asn Val Tyr Val Arg Val  Thr Asn Glu Val Lys  Ser Val Asn
                995             1000            1005
Ile Met  Leu Gln Glu Gln Gly  Ser Ala Tyr Pro Lys  Leu Glu Ala
                1010            1015           1020
Thr Phe Thr Asn Pro Ala Asp  Asn Leu Gln His Leu  Asn Asp Gly
                1025            1030           1035
Ile Lys Ser Tyr Thr Asn Asn  Pro Val Asn Arg Trp  Thr Asn Trp
                1040            1045           1050
Thr Arg Thr Pro Arg Asp Ala  Gly Asp Ser Ile Thr  Val Asn Phe
                1055            1060           1065
Gly Lys Lys His Val Ile Asn  Asn Leu Asp Leu Phe  Val Phe Thr
                1070            1075           1080
Asp Ser Gly Thr Val Val Pro  Glu Lys Ala Glu Val  Gln Tyr Trp
                1085            1090           1095
Asp Gly Thr Ala Trp Lys Asp  Val Glu Asn Leu Thr  Gln Pro Ser
                1100            1105           1110
Pro Tyr Val Val Glu Lys Asn  Glu Leu Thr Phe Asp  Ala Val Ala
                1115            1120           1125
Thr Glu Lys Leu Lys Phe His  Leu Thr Pro Ser Val  Lys Gly Lys
                1130            1135           1140
Phe Leu Ala Leu Thr Glu Ala  Glu Val Tyr Ala Asp  Gln Ile Val
                1145            1150           1155
```

```
Met Gly Glu Thr Ala Lys Leu Gln Ser Ile Thr Val Asn Gly Lys
    1160                1165                1170

Ala Leu Glu Gly Phe Asp His Ala Lys Lys Asn Tyr Glu Leu Val
    1175                1180                1185

Leu Pro Tyr Gly Ser Glu Leu Pro Lys Ile Glu Ala Ala Ala
    1190                1195                1200

Asp Asn Ala Thr Val Thr Ile Leu Pro Ala Phe Ser Tyr Pro Gly
    1205                1210                1215

Thr Ala Lys Leu Phe Val Thr Ser Glu Asp Gly Lys Val Thr Thr
    1220                1225                1230

Glu Tyr Ser Ile Gly Val Ser Thr Glu Glu Pro Lys Leu Val Ser
    1235                1240                1245

Ala

<210> SEQ ID NO 4
<211> LENGTH: 847
<212> TYPE: PRT
<213> ORGANISM: Bacillus circulans

<400> SEQUENCE: 4

Met Lys Lys Ala Ile Ser Cys Val Phe Leu Ile Ser Ala Leu Ile Leu
 1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270
```

```
Thr Val Thr Pro Phe Glu Gln Asn Thr Val Ile Lys Gln Pro Lys Leu
            275                 280                 285

Trp Ser Ile Asp Lys Pro Tyr Arg Tyr Asn Leu Val Thr Glu Val Ile
        290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                    325                 330                 335

Met Lys Leu His Gly Val Ser Met His His Asp Leu Gly Ala Leu Gly
                340                 345                 350

Ala Ala Thr Asn Ala Arg Gly Val Glu Arg Gln Met Gln Ile Met Lys
                355                 360                 365

Asp Met Gly Val Asn Ala Ile Arg Val Thr His Asn Pro Ala Ser Pro
            370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                    405                 410                 415

Phe Phe Asn Ala Trp Ala Glu His Asp Ile Lys Glu Met Val Asp Arg
                420                 425                 430

Gly Lys Asn Glu Pro Ala Ile Ile Met Trp Ser Ile Gly Asn Glu Ile
                435                 440                 445

Tyr Asp Thr Thr Asn Ala Ala Gly Val Glu Thr Ala Arg Asn Leu Val
            450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                    485                 490                 495

Ile Lys Glu Ile Phe Asn Ile Val Asp Val Val Gly Leu Asn Tyr Ser
                500                 505                 510

Glu Asn Asn Tyr Asp Gly Tyr His Lys Gln Asn Pro Ser Trp Lys Leu
            515                 520                 525

Tyr Gly Ser Glu Thr Ser Ser Ala Thr Arg Ser Arg Gly Val Tyr Thr
            530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                    565                 570                 575

Ala Trp Lys Tyr Asp Arg Asp Leu Lys His Ile Ala Gly Gln Phe Ile
                580                 585                 590

Trp Thr Gly Phe Asp Tyr Ile Gly Glu Pro Thr Pro Tyr Tyr Asn Ser
            595                 600                 605

Tyr Pro Ala Lys Ser Ser Tyr Phe Gly Ala Val Asp Thr Ala Gly Phe
            610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                    645                 650                 655

Arg Val Leu Ala Tyr Thr Asn Ala Ser Lys Val Glu Leu Val Leu Asn
                660                 665                 670

Gly Glu Ser Leu Gly Glu Lys Asn Tyr Asp Asn Lys Gln Thr Ser Trp
            675                 680                 685
```

-continued

```
Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
            820                 825                 830

Ala Gly Leu Ser Ser Asp Ser Thr Ser Val Phe Thr Val Thr Pro
        835                 840                 845
```

<210> SEQ ID NO 5
<211> LENGTH: 5214
<212> TYPE: DNA
<213> ORGANISM: Bacillus circulans

<400> SEQUENCE: 5

```
gtgaaaaaag cgattagctg cgttttttta atttcagcac tgattctatc aagctttcaa      60
gtccctgtac agggacaagc catgtcaaaa acgacatcgg cagcaggaaa cagtgtgagc     120
tatgatggag agagacgagt gaattttaac gagaattggc gatttcaacg agaaaccaat     180
ggaagtattg ccgagcacac gaatcctggc tttgacgatt cctcctggcg gaaattaaat     240
ctgccgcatg actggagtat tgaattagat tttaataaaa attctcttgc cacacatgaa     300
ggcggttatt tggacggcgg aatcggctgg taccgaaaaa cctttacaat cccggaatcg     360
atgaagggaa aacgaatttc gcttgatttt gatggcgttt acatgaacag caccacctat     420
ctaaacgggg aagtgctcgg gacctatccg tttggttata atgccttttc ctatgatatt     480
tccgacaaac tttataaaga tggcagggcg aatgtccttg ttgtcaaagt caataacacc     540
cagccgagca gccgctggta ttcggggagc gggatctacc ggaatgtcta tctcactgtg     600
accgatccca tccatgtggc tcgctacgga acatttgtga caacacccaa tttagagaaa     660
tcgataaaag aagacagggc tgatgtgaac atcaagacga aaatcagtaa cgatgctgct     720
gaggcgaaac aggtaaagat taaatcaacc atctacgatg gggctgggaa caccgtacag     780
acagtggaaa cggaggaaaa aacagctgcc gccggcacgg tgactccgtt cgaacaaaac     840
acagtcatca agcagccgaa gctttggagc attgacaagc cttatcgata taaccttgtt     900
acagaagtca tcgttggcgg gcaaacggtg gatacgtatg aaacaaaatt tggtgtcagg     960
tatttcaaat ttgatgaaaa cgaaggcttt tccttaaatg gagagtatat gaagctgcac    1020
ggcgtttcga tgcaccatga tttaggggcg cttggggcgg caacgaatgc acgcggcgtg    1080
gaaagacaaa tgcagattat gaaggatatg ggggtcaatg ccatcagggt tacccacaac    1140
ccggcatcac cggaactgct ggaggcagct aataaattag gctattcat catcgaggag    1200
gcatttgaca gctgggccca gtcaaagaaa ccctatgact atggccgttt tttcaatgca    1260
```

```
tgggctgagc acgacattaa ggaaatggtc gatcggggca aaaacgaacc agctattatc    1320
atgtggtcga tcggaaatga aatatatgat acgaccaatg ccgctggtgt ggaaacagca    1380
cgaaatttag tgggttgggt aaaagaaatt gacaccacaa ggccgacaac gatcggcgag    1440
gataaaaccc gcggagacaa agtaaatgtt acacctatca acagctacat caaggagatt    1500
tttaatattg tcgatgtggt cggactgaac tacagcgaga caactatga tggctaccac     1560 aagcagaatc cgtcatggaa gctgtacggc tcggagacgt cctcggcaac ccgttcgcgt    1620
ggtgtctaca cgcatccgta ccagtataac caaagcacaa agtatgctga tttacagcaa    1680
tcctcttatg acaatgacta tgtcggctgg ggacgaactg cagaagatgc atggaaatat    1740
gaccgcgacc tgaagcatat tgcagggcaa tttatctgga ccggctttga ttatattggc    1800
gagccgacgc catattataa ttcctatcct gcaaaaagct cctatttttgg tgctgtggat   1860 acggctggtt ttccaaagga tattttctac tattaccaaa gccaatggaa aaaggagcct    1920
atggtccacc tgctgccgca ttggaactgg aaggaagggg aaaaggtccg cgtcttagct    1980
tataccaatg caagtaaggt tgaacttgtt ctaaatggtg aatcgttagg ggagaagaac    2040
tatgacaaca aacaaacctc ctggggagca ccatacaaag aaacaaagga tggaaaaacc    2100
tatttggagt gggccgtacc atttaaaccg ggcaaattag aagccgtcgc caaggatgaa    2160
aacggcaaag tgatcgcccg cgatcaggta gtgaccgctg gtgagccagc ctctgtcaga    2220
ttaacggctg atcgtaaggt ggtcaaggcg gacggtacgg atctgtcgtt tattacagca    2280
gacattgttg atagtaaagg gattgttgtc ccggatgccg atcatctgat tacatttaac    2340
gtaacgggcc aaggggaatt ggccggggtt gataacggaa acgcgtccag tgtggagcgt    2400
tacaaggaca caagcgcaa ggctttcagc gggaaagcat tggcgattgt tcaatcaagt     2460
aagctttctg gaaaaattac ggtccatgcg tcagtggcag ggctttcgag cgattccacg    2520
agcgtattta cggtaacgcc agctgaccat gacaaaaaga ttgtagctgg gattgatgat    2580
gttaacctta ctgtcgatgt caatgaagca ccaaagcttc cttcagaaat caaggtttat    2640
tacagtgatg agagtgcagc tgcgaagaat gtgacttggg atgaggtgga tccaaagcag    2700
tacagcactg ttggtgaatt cacagtggaa ggcagtgtcg agggaacttc gctgaaggca    2760
aaggcatttg ttattgtcaa aggaattgtc gccgtcaagc cttattcaac ggcaacaaag    2820
gttggtgtac agccggtgct gcctgaaaaa gcaacccttc tttacagtga tggaacaacc    2880
aagggagcaa ctgtcacgtg ggatgagatc cctgaggaca agctggcaaa agagggccgg    2940
tttaccgtcg agggcagtgt ggagggaaca gacctcaagg ctaatgtcta tgtcagggtg    3000
acaaatgaag taaaatcagt gaatattatg cttcaggagc agggttcagc ttatccaaag    3060
ctcgaagcta cttttaccaa tccagctgac aatcttcagc atttgaacga tggcatcaag    3120
agctatacca ataacccggt caaccgctgg acgaactgga caagaacacc gcgtgatgct    3180
ggtgactcga ttacagttaa ttttggcaag aagcatgtga ttaataatct agatttattt    3240
gtttttaccg acagcggcac ggtggttcca gaaaaggcag aggtccaata ttgggatgga    3300
acggcgtgga aggatgtcga aaatctaaca cagccatcgc catatgtggt agagaaaaat    3360
gaacttacat ttgatgcggt cgcgacagaa aagctgaaat tccatttgac accatctgtg    3420
aaagggaaat tcctagctct aacggaagca gaggtgtacg ccgatcagat tgtgatgggt    3480
gaaacagcaa aacttcaaag tattacggtg aatgggaaag cattagaagg ctttgatcac    3540
gctaaaaaga attatgaact tgtacttcca tatggaagcg agcttcctaa gattgaggcg    3600
```

```
gctgctgccg acaatgcaac tgtcaccatt ttaccggcat tctcctatcc gggaacagca      3660
aaactatttg tcacttcaga ggatgggaag gtaactactg agtacagtat tggtgtttct      3720
acagaagagc caaagctcgt ctccgcagag ttatccgcgg acaagacgaa tgtcatggag      3780
gacgatatca tcgatctgaa ggtaattggt ctcttcgaaa gcaaggaaaa gattgatgtg      3840
accgacagcc agccgacata tgaatttgac cagcagatta ttaaaattga aggcaataag      3900
ctgtatgcgc tggaaacagg aaatgtcaag gtgaaagtga cggtgacata taagggtgtg      3960
agtgtcacaa cacctgcgct tgagtttacg atcgcgaaaa accctgctcc aaaatacatt      4020
acgagcttag agcctgtcac ggttgttgtt aaaaaaggag aagcgccgga gcttccagca      4080
acggttgtgg cccattataa ccgaggaatc ccgcgggatg ttaaggtgaa gtgggaaaga      4140
atcaatccgt ctaagtacca gcagctaggc gagtttaccg tatctggcat ggtgaagggg      4200
accgatataa aagcccaagc aaaagtgatt gtaaaagggg ctgttgcggt cgaggatatt      4260
agaatggctg tgctgttaaa gcaaatgcca cagctgccgg gcaaggttac agtctattat      4320
agtgacggag cggaagaaca aagagcggtc aagtgggagg aaatcccgca ggaggaactc      4380
gagaatgtcg gtaatttaa ggttaaaggt gatgttaatg gagtgaagct gaaagcaaca      4440
gccactattc gagtaaccga tgaagtcggc ggcgagcaga atatcagccg ggctaaaaat      4500
ggttatgaat acccgaaggc tgaagcttcc tttaccaaca atggccctgg atcaagcgat      4560
cgaatcgagg ccatcaatga tgacgtgatc tcctacgagg ctaatccgca taatcgctgg      4620
acgaattggc agccggtacc gcgtgcaggg gactgggttt ctatcaccct tggagactat      4680
gagcctacga aatatgatgt tgatagcatg gagatccact ggttcgcgga tcatgggacc      4740
tcgtatccag agcgtttcca aatcgaatat aaatccggtg atagctggaa ggaagtcacc      4800
agcctgaaaa gcgatccagc ctctccggcc ttgggtaagg caaatgtcta tagctttgat      4860
cgagtaaaaa catcggctat acgagtgaaa atgacagcac aagccggcaa aagcttagcc      4920
attaccgagc tgaaagtatt ttcaaaatgg ccaaaggcag gtaccgaacc agaggtgacc      4980
gatattaagg tcggaggaaa atcgattctg gaggactttg aacaaaaagg cgatcactat      5040
gaagtaacga ttgatgcagg agatgcgaat gtaatgccga aaatcaatgt aaaggctaag      5100
gaccagacga gtattacgat tgtgccagca gttacctctc catccacggc aaaggtaatt      5160
gctaaatccg aggatggcaa gaaagtgaag gtctatagca ttcactataa ataa          5214
```

<210> SEQ ID NO 6
<211> LENGTH: 4266
<212> TYPE: DNA
<213> ORGANISM: Bacillus circulans

<400> SEQUENCE: 6

```
gtgaaaaaag cgattagctg cgttttttta atttcagcac tgattctatc aagctttcaa       60
gtccctgtac agggacaagc catgtcaaaa acgacatcgg cagcaggaaa cagtgtgagc      120
tatgatggag agagacgagt gaattttaac gagaattggc gatttcaacg agaaaccaat      180
ggaagtattg ccggagcaca gaatcctggc tttgacgatt cctcctggcg gaaattaaat      240
ctgccgcatg actggagtat tgaattagat tttaataaaa attctcttgc cacacatgaa      300
ggcggttatt tggacggcgg aatcggctgg taccgaaaaa cctttacaat cccggaatcg      360
atgaagggaa aacgaatttc gcttgatttt gatggcgttt acatgaacag caccacctat      420
ctaaacgggg aagtgctcgg gacctatccg tttggttata atgcctttc ctatgatatt      480 tccgacaaac tttataaaga tggcagggcg aatgtccttg ttgtcaaagt caataacacc      540
```

```
cagccgagca gccgctggta ttcggggagc gggatctacc ggaatgtcta tctcactgtg    600
accgatccca tccatgtggc tcgctacgga acatttgtga caacacccaa tttagagaaa    660
tcgataaaag aagacagggc tgatgtgaac atcaagacga aaatcagtaa cgatgctgct    720
gaggcgaaac aggtaaagat taaatcaacc atctacgatg gggctgggaa caccgtacag    780
acagtggaaa cggaggaaaa aacagctgcc gccggcacgg tgactccgtt cgaacaaaac    840
acagtcatca agcagccgaa gctttggagc attgacaagc cttatcgata taaccttgtt    900
acagaagtca tcgttggcgg gcaaacggtg gatacgtatg aaacaaaatt tggtgtcagg    960
tatttcaaat ttgatgaaaa cgaaggcttt tccttaaatg gagagtatat gaagctgcac   1020
ggcgtttcga tgcaccatga tttaggggcg cttggggcgg caacgaatgc acgcggcgtg   1080
gaaagacaaa tgcagattat gaaggatatg ggggtcaatg ccatcagggt tacccacaac   1140
ccggcatcac cggaactgct ggaggcagct aataaattag gctattcat catcgaggag    1200 gcatttgaca gctgggccca gtcaaagaaa ccctatgact atggccgttt tttcaatgca   1260
tgggctgagc acgacattaa ggaaatggtc gatcggggca aaaacgaacc agctattatc   1320
atgtggtcga tcggaaatga aatatatgat acgaccaatg ccgctggtgt ggaaacagca   1380
cgaaatttag tggggttgggt aaaagaaatt gacaccacaa ggccgacaac gatcggcgag   1440
gataaaaccc gcggagacaa agtaaatgtt acacctatca acagctacat caaggagatt   1500
tttaatattg tcgatgtggt cggactgaac tacagcgaga caactatga tggctaccac    1560 aagcagaatc cgtcatggaa gctgtacggc tcggagacgt cctcggcaac ccgttcgcgt    1620
ggtgtctaca cgcatccgta ccagtataac caaagcacaa agtatgctga tttacagcaa   1680
tcctcttatg acaatgacta tgtcggctgg ggacgaactg cagaagatgc atggaaatat   1740
gaccgcgacc tgaagcatat tgcagggcaa tttatctgga ccggctttga ttatattggc   1800
gagccgacgc catattataa ttcctatcct gcaaaaagct cctattttgg tgctgtggat   1860
acggctggtt ttccaaagga tatttttctac tattaccaaa gccaatggaa aaaggagcct   1920
atggtccacc tgctgccgca ttggaactgg aaggaagggg aaaaggtccg cgtcttagct   1980
tataccaatg caagtaaggt tgaacttgtt ctaaatggtg aatcgttagg ggagaagaac   2040
tatgacaaca aacaaacctc ctggggagca ccatacaaag aaacaaagga tggaaaaacc   2100
tatttggagt gggccgtacc atttaaaccg ggcaaattag aagccgtcgc caaggatgaa   2160
aacggcaaag tgatcgcccg cgatcaggta gtgaccgctg gtgagccagc ctctgtcaga   2220
ttaacggctg atcgtaaggt ggtcaaggcg gacggtacgg atctgtcgtt tattacagca   2280
gacattgttg atagtaaagg gattgttgtc ccggatgccg atcatctgat tacatttaac   2340
gtaacgggcc aaggggaatt ggccggggtt gataacggaa acgcgtccag tgtggagcgt   2400
tacaaggaca caagcgcaa ggctttcagc gggaaagcat ggcgattgt tcaatcaagt    2460 aagctttctg gaaaaattac ggtccatgcg tcagtggcag ggctttcgag cgattccacg   2520 agcgtatttta cggtaacgcc agctgaccat gacaaaaaga ttgtagctgg gattgatgat   2580
gttaacctta ctgtcgatgt caatgaagca ccaaagcttc cttcagaaat caaggtttat    2640
tacagtgatg agagtgcagc tgcgaagaat gtgacttggg atgaggtgga tccaaagcag   2700
tacagcactg ttggtgaatt cacagtggaa ggcagtgtcg agggaacttc gctgaaggca   2760
aaggcatttg ttattgtcaa aggaattgtc gccgtcaagc cttattcaac ggcaacaaag   2820
gttggtgtac agccggtgct gcctgaaaaa gcaaccctc tttacagtga tggaacaacc    2880
```

| aagggagcaa | ctgtcacgtg | ggatgagatc | cctgaggaca | agctggcaaa | agagggccgg | 2940 |
| tttaccgtcg | agggcagtgt | ggagggaaca | gacctcaagg | ctaatgtcta | tgtcagggtg | 3000 |
| acaaatgaag | taaaatcagt | gaatattatg | cttcaggagc | agggttcagc | ttatccaaag | 3060 |
| ctcgaagcta | cttttaccaa | tccagctgac | aatcttcagc | atttgaacga | tggcatcaag | 3120 |
| agctatacca | ataacccggt | caaccgctgg | acgaactgga | caagaacacc | gcgtgatgct | 3180 |
| ggtgactcga | ttacagttaa | ttttggcaag | aagcatgtga | ttaataatct | agatttattt | 3240 |
| gtttttaccg | acagcggcac | ggtggttcca | gaaaaggcag | aggtccaata | ttgggatgga | 3300 |
| acggcgtgga | aggatgtcga | aaatctaaca | cagccatcgc | catatgtggt | agagaaaaat | 3360 |
| gaacttacat | ttgatgcggt | cgcgacagaa | aagctgaaat | ccatttgac | accatctgtg | 3420 |
| aaagggaaat | tcctagctct | aacggaagca | gaggtgtacg | ccgatcagat | tgtgatgggt | 3480 |
| gaaacagcaa | aacttcaaag | tattacggtg | aatgggaaag | cattagaagg | ctttgatcac | 3540 |
| gctaaaaaga | attatgaact | tgtacttcca | tatggaagcg | agcttcctaa | gattgaggcg | 3600 |
| gctgctgccg | acaatgcaac | tgtcaccatt | ttaccggcat | tctcctatcc | gggaacagca | 3660 |
| aaactatttg | tcacttcaga | ggatgggaag | gtaactactg | agtacagtat | tggtgtttct | 3720 |
| acagaagagc | caaagctcgt | ctccgcagag | ttatccgcgg | acaagacgaa | tgtcatggag | 3780 |
| gacgatatca | tcgatctgaa | ggtaattggt | ctcttcgaaa | gcaaggaaaa | gattgatgtg | 3840 |
| accgacagcc | agccgacata | tgaatttgac | cagcagatta | ttaaaattga | aggcaataag | 3900 |
| ctgtatgcgc | tggaaacagg | aaatgtcaag | gtgaaagtga | cggtgacata | taagggtgtg | 3960 |
| agtgtcacaa | cacctgcgct | tgagtttacg | atcgcgaaaa | accctgctcc | aaaatacatt | 4020 |
| acgagcttag | agcctgtcac | ggttgttgtt | aaaaaaggag | aagcgccgga | gcttccagca | 4080 |
| acggttgtgg | cccattataa | ccgaggaatc | ccgcgggatg | ttaaggtgaa | gtgggaagga | 4140 |
| atcaatccgt | ctaagtacca | gcagctaggc | gagtttaccg | tatctggcat | ggtggaaggg | 4200 |
| accgatataa | aagcccaagc | aaaagtgatt | gtaaaagggg | ctgttgcggt | cgaggatatt | 4260 |
| agaatg | | | | | | 4266 |

<210> SEQ ID NO 7
<211> LENGTH: 3747
<212> TYPE: DNA
<213> ORGANISM: Bacillus circulans

<400> SEQUENCE: 7

| gtgaaaaaag | cgattagctg | cgttttttta | atttcagcac | tgattctatc | aagctttcaa | 60 |
| gtccctgtac | agggacaagc | catgtcaaaa | acgacatcgg | cagcaggaaa | cagtgtgagc | 120 |
| tatgatggag | agagacagt | gaattttaac | gagaattggc | gatttcaacg | agaaaccaat | 180 |
| ggaagtattg | ccggagcaca | gaatcctggc | tttgacgatt | cctcctggcg | gaaattaaat | 240 |
| ctgccgcatg | actggagtat | tgaattagat | tttaataaaa | attctcttgc | cacacatgaa | 300 |
| ggcggttatt | tggacggcgg | aatcggctgg | taccgaaaaa | cctttacaat | cccggaatcg | 360 |
| atgaagggaa | aacgaatttc | gcttgatttt | gatggcgttt | acatgaacag | caccacctat | 420 |
| ctaaacgggg | aagtgctcgg | gacctatccg | tttggttata | atgccttttc | ctatgatatt | 480 |
| tccgacaaac | tttataaaga | tggcagggcg | aatgtccttg | ttgtcaaagt | caataacacc | 540 |
| cagccgagca | gccgctggta | ttcggggagc | gggatctacc | ggaatgtcta | tctcactgtg | 600 |
| accgatccca | tccatgtggc | tcgctacgga | acatttgtga | caacacccaa | tttagagaaa | 660 |
| tcgataaaag | aagacagggc | tgatgtgaac | atcaagacga | aaatcagtaa | cgatgctgct | 720 |

```
gaggcgaaac aggtaaagat taaatcaacc atctacgatg gggctgggaa caccgtacag    780
acagtggaaa cggaggaaaa aacagctgcc gccggcacgg tgactccgtt cgaacaaaac    840
acagtcatca agcagccgaa gctttggagc attgacaagc cttatcgata taaccttgtt    900
acagaagtca tcgttggcgg gcaaacggtg gatacgtatg aaacaaaatt tggtgtcagg    960
tatttcaaat ttgatgaaaa cgaaggcttt tccttaaatg gagagtatat gaagctgcac   1020
ggcgtttcga tgcaccatga tttaggggcg cttggggcgg caacgaatgc acgcggcgtg   1080
gaaagacaaa tgcagattat gaaggatatg ggggtcaatg ccatcagggt tacccacaac   1140
ccggcatcac cggaactgct ggaggcagct aataaattag gctattcat catcgaggag    1200 gcatttgaca gctgggccca gtcaaagaaa ccctatgact atggccgttt tttcaatgca   1260
tgggctgagc acgacattaa ggaaatggtc gatcggggca aaaacgaacc agctattatc   1320
atgtggtcga tcggaaatga aatatatgat acgaccaatg ccgctggtgt ggaaacagca   1380
cgaaatttag tggttgggt aaaagaaatt gacaccacaa ggccgacaac gatcggcgag   1440
gataaaaccc gcggagacaa agtaaatgtt acacctatca acagctacat caaggagatt   1500
tttaatattg tcgatgtggt cggactgaac tacagcgaga caactatga tggctaccac    1560 aagcagaatc cgtcatggaa gctgtacggc tcggagacgt cctcggcaac ccgttcgcgt   1620
ggtgtctaca cgcatccgta ccagtataac caaagcacaa gtatgctga tttacagcaa    1680 tcctcttatg acaatgacta tgtcggctgg ggacgaactg cagaagatgc atggaaatat   1740
gaccgcgacc tgaagcatat tgcagggcaa tttatctgga ccggctttga ttatattggc   1800
gagccgacgc catattataa ttcctatcct gcaaaaagct cctattttgg tgctgtggat   1860
acggctggtt ttccaaagga tattttctac tattaccaaa gccaatggaa aaaggagcct   1920
atggtccacc tgctgccgca ttggaactgg aaggaagggg aaaaggtccg cgtcttagct   1980
tataccaatg caagtaaggt tgaacttgtt ctaaatggtg aatcgttagg ggagaagaac   2040
tatgacaaca aacaaacctc ctggggagca ccatacaaag aaacaaagga tggaaaaacc   2100
tatttggagt gggccgtacc atttaaaccg ggcaaattag aagccgtcgc caaggatgaa   2160
aacggcaaag tgatcgcccg cgatcaggta gtgaccgctg gtgagccagc ctctgtcaga   2220
ttaacggctg atcgtaaggt ggtcaaggcg gacggtacgg atctgtcgtt tattacagca   2280
gacattgttg atagtaaagg gattgttgtc ccggatgccg atcatctgat tacattaac    2340 gtaacgggcc aaggggaatt ggccgggggtt gataacggaa acgcgtccag tgtggagcgt   2400
tacaaggaca caagcgcaa ggcttttcagc gggaaagcat tggcgattgt tcaatcaagt   2460
aagctttctg gaaaaattac ggtccatgcg tcagtggcag ggctttcgag cgattccacg   2520
agcgtattta cggtaacgcc agctgaccat gacaaaaaga ttgtagctgg gattgatgat   2580
gttaacctta ctgtcgatgt caatgaagca ccaaagcttc cttcagaaat caaggtttat   2640
tacagtgatg agagtgcagc tgcgaagaat gtgacttggg atgaggtgga tccaaagcag   2700
tacagcactg ttggtgaatt cacagtggaa ggcagtgtcg agggaacttc gctgaaggca   2760
aaggcatttg ttattgtcaa aggaattgtc gccgtcaagc cttattcaac ggcaacaaag   2820
gttggtgtac agccggtgct gcctgaaaaa gcaacccttc tttacagtga tggaacaacc   2880
aagggagcaa ctgtcacgtg ggatgagatc cctgaggaca agctggcaaa agagggccgg   2940
tttaccgtcg agggcagtgt ggagggaaca gacctcaagg ctaatgtcta tgtcagggtg   3000
acaaatgaag taaaatcagt gaatattatg cttcaggagc agggttcagc ttatccaaag   3060
```

```
ctcgaagcta cttttaccaa tccagctgac aatcttcagc atttgaacga tggcatcaag      3120
agctatacca ataacccggt caaccgctgg acgaactgga caagaacacc gcgtgatgct      3180
ggtgactcga ttacagttaa ttttggcaag aagcatgtga ttaataatct agatttattt      3240
gtttttaccg acagcggcac ggtggttcca gaaaaggcag aggtccaata ttgggatgga      3300
acggcgtgga aggatgtcga aaatctaaca cagccatcgc catatgtggt agagaaaaat      3360
gaacttacat tgatgcggt cgcgacagaa aagctgaaat tccatttgac accatctgtg      3420
aaagggaaat tcctagctct aacggaagca gaggtgtacg ccgatcagat tgtgatgggt      3480
gaaacagcaa aacttcaaag tattacggtg aatgggaaag cattagaagg ctttgatcac      3540
gctaaaaaga attatgaact tgtacttcca tatggaagcg agcttcctaa gattgaggcg      3600
gctgctgccg acaatgcaac tgtcaccatt ttaccggcat tctcctatcc gggaacagca      3660
aaactatttg tcacttcaga ggatgggaag gtaactactg agtacagtat tggtgtttct      3720
acagaagagc aaagctcgt ctccgca                                          3747

<210> SEQ ID NO 8
<211> LENGTH: 2541
<212> TYPE: DNA
<213> ORGANISM: Bacillus circulans

<400> SEQUENCE: 8
gtgaaaaaag cgattagctg cgttttttta atttcagcac tgattctatc aagctttcaa        60
gtccctgtac agggacaagc catgtcaaaa acgacatcgg cagcaggaaa cagtgtgagc       120
tatgatggag agagacgagt gaattttaac gagaattggc gatttcaacg agaaaccaat       180
ggaagtattg ccggagcaca gaatcctggc tttgacgatt cctcctggcg gaaattaaat       240
ctgccgcatg actggagtat tgaattagat tttaataaaa attctcttgc cacacatgaa       300
ggcggttatt tggacggcgg aatcggctgg taccgaaaaa cctttacaat cccggaatcg       360
atgaagggaa aacgaatttc gcttgatttt gatggcgttt acatgaacag caccaccctat      420 ctaaacgggg aagtgctcgg gacctatccg tttggttata tgccttttc ctatgatatt        480 tccgacaaac tttataaaga tggcagggcg aatgtccttg ttgtcaaagt caataacacc       540
cagccgagca gccgctggta ttcggggagc gggatctacc ggaatgtcta tctcactgtg       600
accgatccca tccatgtggc tcgctacgga acatttgtga caacacccaa tttagagaaa       660
tcgataaaag aagacagggc tgatgtgaac atcaagacga aatcagtaa cgatgctgct       720 gaggcgaaac aggtaaagat taaatcaacc atctacgatg gggctgggaa caccgtacag       780
acagtggaaa cggaggaaaa aacagctgcc gccggcacgg tgactccgtt cgaacaaaac       840
acagtcatca gcagccgaa gctttggagc attgacaagc cttatcgata taaccttgtt       900
acagaagtca tcgttggcgg gcaaacggtg gatacgtatg aaacaaaatt tggtgtcagg       960
tatttcaaat ttgatgaaaa cgaaggcttt tccttaaatg gagagtatat gaagctgcac      1020
ggcgtttcga tgcaccatga tttaggggcg cttggggcgg caacgaatgc acgcggcgtg      1080
gaaagacaaa tgcagattat gaaggatatg ggggtcaatg ccatcagggt tacccacaac      1140
ccggcatcac cggaactgct ggaggcagct aataaattag gctattcat catcgaggag      1200 gcatttgaca gctgggccca gtcaaagaaa ccctatgact atggccgttt tttcaatgca      1260
tgggctgagc acgacattaa ggaaatggtc gatcggggca aaacgaacc agctattatc      1320 atgtggtcga tcgaaatga aatatatgat acgaccaatg ccgctggtgt ggaaacagca      1380
cgaaatttag tgggttgggt aaaagaaatt gacaccacaa ggccgacaac gatcggcgag      1440
```

-continued

```
gataaaaccc gcggagacaa agtaaatgtt acacctatca acagctacat caaggagatt    1500
tttaatattg tcgatgtggt cggactgaac tacagcgaga acaactatga tggctaccac    1560
aagcagaatc cgtcatggaa gctgtacggc tcggagacgt cctcggcaac ccgttcgcgt    1620
ggtgtctaca cgcatccgta ccagtataac caaagcacaa agtatgctga tttacagcaa    1680
tcctcttatg acaatgacta tgtcggctgg ggacgaactg cagaagatgc atggaaatat    1740
gaccgcgacc tgaagcatat tgcagggcaa tttatctgga ccggctttga ttatattggc    1800
gagccgacgc catattataa ttcctatcct gcaaaaagct cctattttgg tgctgtggat    1860
acggctggtt ttccaaagga tattttctac tattaccaaa gccaatggaa aaaggagcct    1920
atggtccacc tgctgccgca ttggaactgg aaggaagggg aaaaggtccg cgtcttagct    1980
tataccaatg caagtaaggt tgaacttgtt ctaaatggtg aatcgttagg ggagaagaac    2040
tatgacaaca aacaaaccct ctggggagca ccatacaaag aaacaaagga tggaaaaacc    2100
tatttggagt gggccgtacc atttaaaccg ggcaaattag aagccgtcgc caaggatgaa    2160
aacggcaaag tgatcgcccg cgatcaggta gtgaccgctg gtgagccagc ctctgtcaga    2220
ttaacggctg atcgtaaggt ggtcaaggcg acggtacgg atctgtcgtt tattacagca    2280
gacattgttg atagtaaagg gattgttgtc ccggatgccg atcatctgat tacatttaac    2340
gtaacgggcc aaggggaatt ggccggggtt gataacggaa acgcgtccag tgtggagcgt    2400
tacaaggaca acaagcgcaa ggctttcagc gggaaagcat ggcgattgt tcaatcaagt    2460 aagctttctg gaaaaattac ggtccatgcg tcagtggcag ggctttcgag cgattccacg    2520 agcgtatta cggtaacgcc a                                               2541
```

<210> SEQ ID NO 9
<211> LENGTH: 847
<212> TYPE: PRT
<213> ORGANISM: Artificial Sequence
<220> FEATURE:
<223> OTHER INFORMATION: Modified enzyme

<400> SEQUENCE: 9

```
Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160
```

-continued

```
Ser Asp Lys Leu Tyr Pro Asp Gly Arg Ala Asn Val Leu Val Val Lys
            165                 170                 175
Val Asn Asn Thr Gln Pro Ser Ser Arg Trp Tyr Ser Gly Ser Gly Ile
            180                 185                 190
Tyr Arg Asn Val Tyr Leu Thr Val Thr Asp Pro Ile His Val Ala Arg
            195                 200                 205
Tyr Gly Thr Phe Val Thr Thr Pro Asn Leu Glu Lys Ser Ile Lys Glu
            210                 215                 220
Asp Arg Ala Asp Val Asn Ile Lys Thr Lys Ile Ser Asn Asp Ala Ala
225                 230                 235                 240
Glu Ala Lys Gln Val Lys Ile Lys Ser Thr Ile Tyr Asp Gly Ala Gly
            245                 250                 255
Asn Thr Val Gln Thr Val Glu Thr Glu Lys Thr Ala Ala Ala Gly
            260                 265                 270
Thr Val Thr Pro Phe Glu Gln Asn Thr Val Ile Lys Gln Pro Lys Leu
            275                 280                 285
Trp Ser Ile Asp Lys Pro Tyr Arg Tyr Asn Leu Val Thr Glu Val Ile
            290                 295                 300
Val Gly Gln Thr Val Asp Thr Tyr Glu Thr Lys Phe Gly Val Arg
305                 310                 315                 320
Tyr Phe Lys Phe Asp Glu Asn Glu Gly Phe Ser Leu Asn Gly Glu Tyr
            325                 330                 335
Met Lys Leu His Gly Val Ser Met His His Asp Leu Gly Ala Leu Gly
            340                 345                 350
Ala Ala Thr Asn Ala Arg Gly Val Glu Arg Gln Met Gln Ile Met Lys
            355                 360                 365
Asp Met Gly Val Asn Ala Ile Arg Val Thr His Asn Pro Ala Ser Pro
370                 375                 380
Glu Leu Leu Glu Ala Ala Asn Lys Leu Gly Leu Phe Ile Ile Glu Glu
385                 390                 395                 400
Ala Phe Asp Ser Trp Ala Gln Ser Lys Lys Pro Tyr Tyr Gly Arg
            405                 410                 415
Phe Phe Asn Ala Trp Ala Glu His Asp Ile Lys Glu Met Val Asp Arg
            420                 425                 430
Gly Lys Asn Glu Pro Ala Ile Ile Met Trp Ser Ile Gly Asn Glu Ile
            435                 440                 445
Tyr Asp Thr Thr Asn Ala Ala Gly Val Glu Thr Ala Arg Asn Leu Val
            450                 455                 460
Gly Trp Val Lys Glu Ile Asp Thr Thr Arg Pro Thr Thr Ile Gly Glu
465                 470                 475                 480
Asp Lys Thr Arg Gly Asp Lys Val Asn Val Thr Pro Ile Asn Ser Tyr
            485                 490                 495
Ile Lys Glu Ile Phe Asn Ile Val Asp Val Val Gly Leu Asn Tyr Ser
            500                 505                 510
Glu Asn Asn Tyr Asp Gly Tyr His Lys Gln Asn Pro Ser Trp Lys Leu
            515                 520                 525
Tyr Gly Ser Glu Thr Ser Ser Ala Thr Arg Ser Arg Gly Val Tyr Thr
            530                 535                 540
His Pro Tyr Gln Tyr Asn Gln Ser Thr Lys Tyr Ala Asp Leu Gln Gln
545                 550                 555                 560
Ser Ser Tyr Asp Asn Asp Tyr Val Gly Trp Gly Arg Thr Ala Glu Asp
            565                 570                 575
Ala Trp Lys Tyr Asp Arg Asp Leu Lys His Ile Ala Gly Gln Phe Ile
```

```
                    580                 585                 590
Trp Thr Gly Phe Asp Tyr Ile Gly Glu Pro Thr Pro Tyr Tyr Asn Ser
                595                 600                 605

Tyr Pro Ala Lys Ser Ser Tyr Phe Gly Ala Val Asp Thr Ala Gly Phe
            610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
        690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
            820                 825                 830

Ala Gly Leu Ser Ser Asp Ser Thr Ser Val Phe Thr Val Thr Pro
        835                 840                 845

<210> SEQ ID NO 10
<211> LENGTH: 847
<212> TYPE: PRT
<213> ORGANISM: Artificial Sequence
<220> FEATURE:
<223> OTHER INFORMATION: Modified enzyme

<400> SEQUENCE: 10

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Gly Ile Gly Trp Tyr Arg
```

-continued

```
                100                 105                 110
        Lys Thr Phe Thr Ile Pro Glu Ser Met Lys Gly Lys Arg Ile Ser Leu
                    115                 120                 125

Asp Phe Asp Gly Val Tyr Met Asn Ser Thr Thr Tyr Leu Asn Gly Glu
                    130                 135                 140

Val Leu Gly Thr Tyr Pro Phe Gly Tyr Asn Ala Phe Ser Tyr Asp Ile
        145                 150                 155                 160

Ser Asp Lys Leu Tyr Lys Asp Gly Arg Ala Asn Val Leu Val Val Lys
                        165                 170                 175

Val Asn Asn Thr Gln Pro Ser Ser Arg Trp Tyr Ser Gly Ser Gly Ile
                    180                 185                 190

Tyr Arg Asn Val Tyr Leu Thr Val Thr Asp Pro Ile His Val Ala Arg
                    195                 200                 205

Tyr Gly Thr Phe Val Thr Thr Pro Asn Leu Glu Lys Ser Ile Lys Glu
                    210                 215                 220

Asp Arg Ala Asp Val Asn Ile Lys Thr Lys Ile Ser Asn Asp Ala Ala
        225                 230                 235                 240

Glu Ala Lys Gln Val Lys Ile Lys Ser Thr Ile Tyr Asp Gly Ala Gly
                        245                 250                 255

Asn Thr Val Gln Thr Val Glu Thr Glu Lys Thr Ala Ala Ala Gly
                    260                 265                 270

Thr Val Thr Pro Phe Glu Gln Asn Thr Val Ile Lys Gln Pro Lys Leu
                    275                 280                 285

Trp Ser Ile Asp Lys Pro Tyr Arg Tyr Asn Leu Val Thr Glu Val Ile
                    290                 295                 300

Val Gly Pro Gln Thr Val Asp Thr Tyr Glu Thr Lys Phe Gly Val Arg
        305                 310                 315                 320

Tyr Phe Lys Phe Asp Glu Asn Glu Gly Phe Ser Leu Asn Gly Glu Tyr
                        325                 330                 335

Met Lys Leu His Gly Val Ser Met His His Asp Leu Gly Ala Leu Gly
                    340                 345                 350

Ala Ala Thr Asn Ala Arg Gly Val Glu Arg Gln Met Gln Ile Met Lys
                    355                 360                 365

Asp Met Gly Val Asn Ala Ile Arg Val Thr His Asn Pro Ala Ser Pro
                    370                 375                 380

Glu Leu Leu Glu Ala Ala Asn Lys Leu Gly Leu Phe Ile Ile Glu Glu
        385                 390                 395                 400

Ala Phe Asp Ser Trp Ala Gln Ser Lys Lys Pro Tyr Asp Tyr Gly Arg
                        405                 410                 415

Phe Phe Asn Ala Trp Ala Glu His Asp Ile Lys Glu Met Val Asp Arg
                    420                 425                 430

Gly Lys Asn Glu Pro Ala Ile Ile Met Trp Ser Ile Gly Asn Glu Ile
                    435                 440                 445

Tyr Asp Thr Thr Asn Ala Ala Gly Val Glu Thr Ala Arg Asn Leu Val
                    450                 455                 460

Gly Trp Val Lys Glu Ile Asp Thr Thr Arg Pro Thr Thr Ile Gly Glu
        465                 470                 475                 480

Asp Lys Thr Arg Gly Asp Lys Val Asn Val Thr Pro Ile Asn Ser Tyr
                        485                 490                 495

Ile Lys Glu Ile Phe Asn Ile Val Asp Val Val Gly Leu Asn Tyr Ser
                    500                 505                 510

Glu Asn Asn Tyr Asp Gly Tyr His Lys Gln Asn Pro Ser Trp Lys Leu
                    515                 520                 525
```

Tyr Gly Ser Glu Thr Ser Ser Ala Thr Arg Ser Arg Gly Val Tyr Thr
                530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
                660                 665                 670

Gly Glu Ser Leu Gly Lys Asn Tyr Asp Asn Lys Gln Thr Ser Trp
                675                 680                 685

Gly Ala Pro Tyr Lys Glu Thr Lys Asp Gly Lys Thr Tyr Leu Glu Trp
        690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
                805                 810                 815

Val Gln Ser Ser Lys Leu Ser Gly Lys Ile Thr Val His Ala Ser Val
                820                 825                 830

Ala Gly Leu Ser Ser Asp Ser Thr Ser Val Phe Thr Val Thr Pro
            835                 840                 845

<210> SEQ ID NO 11
<211> LENGTH: 847
<212> TYPE: PRT
<213> ORGANISM: Artificial Sequence
<220> FEATURE:
<223> OTHER INFORMATION: Modified enzyme

<400> SEQUENCE: 11

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
                20                  25                  30

Ser Ala Ala Gly Asn Ser Val Ser Tyr Asp Gly Glu Arg Arg Val Asn
            35                  40                  45

```
Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Lys Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
    195                 200                 205

Tyr Gly Thr Phe Val Thr Thr Pro Asn Leu Glu Lys Ser Ile Lys Glu
210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
            275                 280                 285

Trp Ser Ile Asp Lys Pro Tyr Arg Tyr Asn Leu Val Thr Glu Val Ile
    290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
            435                 440                 445

Tyr Asp Thr Thr Asn Ala Ala Gly Val Glu Thr Ala Arg Asn Leu Val
    450                 455                 460
```

-continued

```
Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
        755                 760                 765

Val Val Pro Asp Ala Asp His Leu Ile Thr Phe Asn Val Thr Gly Gln
    770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Lys Ala Leu Ala Ile
                805                 810                 815

Val Gln Ser Ser Lys Leu Ser Gly Lys Ile Thr Val His Ala Ser Val
            820                 825                 830

Pro Gly Leu Ser Ser Asp Ser Thr Ser Val Phe Thr Val Thr Pro
        835                 840                 845
```

<210> SEQ ID NO 12
<211> LENGTH: 847
<212> TYPE: PRT
<213> ORGANISM: Artificial Sequence
<220> FEATURE:
<223> OTHER INFORMATION: Modified enzyme

<400> SEQUENCE: 12

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
        50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
130                 135                 140

Val Leu Gly Thr Tyr Pro Phe Gly Tyr Asn Ala Phe Ser Tyr Asp Ile
145                 150                 155                 160

Ser Asp Lys Leu Tyr Pro Asp Gly Arg Ala Asn Val Leu Val Lys
            165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
            195                 200                 205

Tyr Gly Thr Phe Val Thr Thr Pro Asn Leu Glu Lys Ser Ile Lys Glu
            210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
            245                 250                 255

Asn Thr Val Gln Thr Val Glu Thr Glu Lys Thr Ala Ala Gly
            260                 265                 270

Thr Val Thr Pro Phe Glu Gln Asn Thr Val Ile Lys Gln Pro Lys Leu
            275                 280                 285

Trp Ser Ile Asp Lys Pro Tyr Arg Tyr Asn Leu Val Thr Glu Val Ile
290                 295                 300

Val Gly Pro Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
            325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
            370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg

```
                    405                 410                 415
Phe Phe Asn Ala Trp Ala Glu His Asp Ile Lys Glu Met Val Asp Arg
                420                 425                 430
Gly Lys Asn Glu Pro Ala Ile Ile Met Trp Ser Ile Gly Asn Glu Ile
            435                 440                 445
Tyr Asp Thr Thr Asn Ala Ala Gly Val Glu Thr Ala Arg Asn Leu Val
        450                 455                 460
Gly Trp Val Lys Glu Ile Asp Thr Thr Arg Pro Thr Thr Ile Gly Glu
465                 470                 475                 480
Asp Lys Thr Arg Gly Asp Lys Val Asn Val Thr Pro Ile Asn Ser Tyr
                485                 490                 495
Ile Lys Glu Ile Phe Asn Ile Val Asp Val Gly Leu Asn Tyr Ser
            500                 505                 510
Glu Asn Asn Tyr Asp Gly Tyr His Lys Gln Asn Pro Ser Trp Lys Leu
        515                 520                 525
Tyr Gly Ser Glu Thr Ser Ser Ala Thr Arg Ser Arg Gly Val Tyr Thr
    530                 535                 540
His Pro Tyr Gln Tyr Asn Gln Ser Thr Lys Tyr Ala Asp Leu Gln Gln
545                 550                 555                 560
Ser Ser Tyr Asp Asn Asp Tyr Val Gly Trp Gly Arg Thr Ala Glu Asp
                565                 570                 575
Ala Trp Lys Tyr Asp Arg Asp Leu Lys His Ile Ala Gly Gln Phe Ile
            580                 585                 590
Trp Thr Gly Phe Asp Tyr Ile Gly Glu Pro Thr Pro Tyr Tyr Asn Ser
        595                 600                 605
Tyr Pro Ala Lys Ser Ser Tyr Phe Gly Ala Val Asp Thr Ala Gly Phe
    610                 615                 620
Pro Lys Asp Ile Phe Tyr Tyr Gln Ser Gln Trp Lys Lys Glu Pro
625                 630                 635                 640
Met Val His Leu Leu Pro His Trp Asn Trp Lys Glu Gly Glu Lys Val
                645                 650                 655
Arg Val Leu Ala Tyr Thr Asn Ala Ser Lys Val Glu Leu Val Leu Asn
            660                 665                 670
Gly Glu Ser Leu Gly Glu Lys Asn Tyr Asp Asn Lys Gln Thr Ser Trp
        675                 680                 685
Gly Ala Pro Tyr Lys Glu Thr Lys Asp Gly Lys Thr Tyr Leu Glu Trp
    690                 695                 700
Ala Val Pro Phe Lys Pro Gly Lys Leu Glu Ala Val Ala Lys Asp Glu
705                 710                 715                 720
Asn Gly Lys Val Ile Ala Arg Asp Gln Val Val Thr Ala Gly Glu Pro
                725                 730                 735
Ala Ser Val Arg Leu Thr Ala Asp Arg Lys Val Val Lys Ala Asp Gly
            740                 745                 750
Thr Asp Leu Ser Phe Ile Thr Ala Asp Ile Val Asp Ser Lys Gly Ile
        755                 760                 765
Val Val Pro Asp Ala Asp His Leu Ile Thr Phe Asn Val Thr Gly Gln
    770                 775                 780
Gly Glu Leu Ala Gly Val Asp Asn Gly Asn Ala Ser Ser Val Glu Arg
785                 790                 795                 800
Tyr Lys Asp Asn Lys Arg Lys Ala Phe Ser Gly Lys Ala Leu Ala Ile
                805                 810                 815
Val Gln Ser Ser Lys Leu Ser Gly Lys Ile Thr Val His Ala Ser Val
            820                 825                 830
```

```
Ala Gly Leu Ser Ser Asp Ser Thr Ser Val Phe Thr Val Thr Pro
        835                 840                 845

<210> SEQ ID NO 13
<211> LENGTH: 847
<212> TYPE: PRT
<213> ORGANISM: Artificial Sequence
<220> FEATURE:
<223> OTHER INFORMATION: Modified enzyme

<400> SEQUENCE: 13

Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
        35                  40                  45

Phe Asn Glu Asn Trp Arg Phe Gln Arg Glu Thr Asn Gly Ser Ile Ala
    50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
            100                 105                 110

Lys Thr Phe Thr Ile Pro Glu Ser Met Lys Gly Lys Arg Ile Ser Leu
        115                 120                 125

Asp Phe Asp Gly Val Tyr Met Asn Ser Thr Thr Tyr Leu Asn Gly Glu
    130                 135                 140

Val Leu Gly Thr Tyr Pro Phe Gly Tyr Asn Ala Phe Ser Tyr Asp Ile
145                 150                 155                 160

Ser Asp Lys Leu Tyr Pro Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
        195                 200                 205

Tyr Gly Thr Phe Val Thr Thr Pro Asn Leu Glu Lys Ser Ile Lys Glu
    210                 215                 220

Asp Arg Ala Asp Val Asn Ile Lys Thr Lys Ile Ser Asn Asp Ala Ala
225                 230                 235                 240

Glu Ala Lys Gln Val Lys Ile Lys Ser Thr Ile Tyr Asp Gly Ala Gly
                245                 250                 255

Asn Thr Val Gln Thr Val Glu Thr Glu Lys Thr Ala Ala Ala Gly
            260                 265                 270

Thr Val Thr Pro Phe Glu Gln Asn Thr Val Ile Lys Gln Pro Lys Leu
        275                 280                 285

Trp Ser Ile Asp Lys Pro Tyr Arg Tyr Asn Leu Val Thr Glu Val Ile
    290                 295                 300

Val Gly Gly Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350
```

```
Ala Ala Thr Asn Ala Arg Gly Val Glu Arg Gln Met Gln Ile Met Lys
            355                 360                 365

Asp Met Gly Val Asn Ala Ile Arg Val Thr His Asn Pro Ala Ser Pro
            370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
                420                 425                 430

Gly Lys Asn Glu Pro Ala Ile Ile Met Trp Ser Ile Gly Asn Glu Ile
            435                 440                 445

Tyr Asp Thr Thr Asn Ala Ala Gly Val Glu Thr Ala Arg Asn Leu Val
            450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
            515                 520                 525

Tyr Gly Ser Glu Thr Ser Ser Ala Thr Arg Ser Arg Gly Val Tyr Thr
            530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
            595                 600                 605

Tyr Pro Ala Lys Ser Ser Tyr Phe Gly Ala Val Asp Thr Ala Gly Phe
            610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
            645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
            675                 680                 685

Gly Ala Pro Tyr Lys Glu Thr Lys Asp Gly Lys Thr Tyr Leu Glu Trp
            690                 695                 700

Ala Val Pro Phe Lys Pro Gly Lys Leu Glu Ala Val Ala Lys Asp Glu
705                 710                 715                 720

Asn Gly Lys Val Ile Ala Arg Asp Gln Val Val Thr Ala Gly Glu Pro
                725                 730                 735

Ala Ser Val Arg Leu Thr Ala Asp Arg Lys Val Val Lys Ala Asp Gly
                740                 745                 750

Thr Asp Leu Ser Phe Ile Thr Ala Asp Ile Val Asp Ser Lys Gly Ile
            755                 760                 765
```

Val Val Pro Asp Ala Asp His Leu Ile Thr Phe Asn Val Thr Gly Gln
770                     775                     780

Gly Glu Leu Ala Gly Val Asp Asn Gly Asn Ala Ser Ser Val Glu Arg
785                     790                     795                     800

Tyr Lys Asp Asn Lys Arg Lys Ala Phe Ser Gly Lys Ala Leu Ala Ile
                    805                     810                     815

Val Gln Ser Ser Lys Leu Ser Gly Lys Ile Thr Val His Ala Ser Val
                    820                     825                     830

Pro Gly Leu Ser Ser Asp Ser Thr Ser Val Phe Thr Val Thr Pro
                    835                     840                     845

<210> SEQ ID NO 14
<211> LENGTH: 847
<212> TYPE: PRT
<213> ORGANISM: Artificial Sequence
<220> FEATURE:
<223> OTHER INFORMATION: Modified enzyme

<400> SEQUENCE: 14

Met Lys Lys Ala Ile Ser Cys Val Phe Leu Ile Ser Ala Leu Ile Leu
1               5                       10                      15

Ser Ser Phe Gln Val Pro Val Gln Gly Gln Ala Met Ser Lys Thr Thr
                20                      25                      30

Ser Ala Ala Gly Asn Ser Val Ser Tyr Asp Gly Glu Arg Arg Val Asn
            35                      40                      45

Phe Asn Glu Asn Trp Arg Phe Gln Arg Glu Thr Asn Gly Ser Ile Ala
        50                      55                      60

Gly Ala Gln Asn Pro Gly Phe Asp Asp Ser Ser Trp Arg Lys Leu Asn
65                      70                      75                      80

Leu Pro His Asp Trp Ser Ile Glu Leu Asp Phe Asn Lys Asn Ser Leu
                    85                      90                      95

Ala Thr His Glu Gly Gly Tyr Leu Asp Gly Ile Gly Trp Tyr Arg
                100                     105                     110

Lys Thr Phe Thr Ile Pro Glu Ser Met Lys Gly Lys Arg Ile Ser Leu
                115                     120                     125

Asp Phe Asp Gly Val Tyr Met Asn Ser Thr Thr Tyr Leu Asn Gly Glu
            130                     135                     140

Val Leu Gly Thr Tyr Pro Phe Gly Tyr Asn Ala Phe Ser Tyr Asp Ile
145                     150                     155                     160

Ser Asp Lys Leu Tyr Lys Asp Gly Arg Ala Asn Val Leu Val Val Lys
                    165                     170                     175

Val Asn Asn Thr Gln Pro Ser Ser Arg Trp Tyr Ser Gly Ser Gly Ile
                180                     185                     190

Tyr Arg Asn Val Tyr Leu Thr Val Thr Asp Pro Ile His Val Ala Arg
                195                     200                     205

Tyr Gly Thr Phe Val Thr Thr Pro Asn Leu Glu Lys Ser Ile Lys Glu
            210                     215                     220

Asp Arg Ala Asp Val Asn Ile Lys Thr Lys Ile Ser Asn Asp Ala Ala
225                     230                     235                     240

Glu Ala Lys Gln Val Lys Ile Lys Ser Thr Ile Tyr Asp Gly Ala Gly
                    245                     250                     255

Asn Thr Val Gln Thr Val Glu Thr Glu Glu Lys Thr Ala Ala Ala Gly
                260                     265                     270

Thr Val Thr Pro Phe Glu Gln Asn Thr Val Ile Lys Gln Pro Lys Leu
                275                     280                     285

```
Trp Ser Ile Asp Lys Pro Tyr Arg Tyr Asn Leu Val Thr Glu Val Ile
    290                 295                 300

Val Gly Pro Gln Thr Val Asp Thr Tyr Glu Thr Lys Phe Gly Val Arg
305                 310                 315                 320

Tyr Phe Lys Phe Asp Glu Asn Glu Gly Phe Ser Leu Asn Gly Glu Tyr
                325                 330                 335

Met Lys Leu His Gly Val Ser Met His His Asp Leu Gly Ala Leu Gly
            340                 345                 350

Ala Ala Thr Asn Ala Arg Gly Val Glu Arg Gln Met Gln Ile Met Lys
        355                 360                 365

Asp Met Gly Val Asn Ala Ile Arg Val Thr His Asn Pro Ala Ser Pro
370                 375                 380

Glu Leu Leu Glu Ala Ala Asn Lys Leu Gly Leu Phe Ile Ile Glu Glu
385                 390                 395                 400

Ala Phe Asp Ser Trp Ala Gln Ser Lys Lys Pro Tyr Asp Tyr Gly Arg
                405                 410                 415

Phe Phe Asn Ala Trp Ala Glu His Asp Ile Lys Glu Met Val Asp Arg
            420                 425                 430

Gly Lys Asn Glu Pro Ala Ile Ile Met Trp Ser Ile Gly Asn Glu Ile
        435                 440                 445

Tyr Asp Thr Thr Asn Ala Ala Gly Val Glu Thr Ala Arg Asn Leu Val
    450                 455                 460

Gly Trp Val Lys Glu Ile Asp Thr Thr Arg Pro Thr Thr Ile Gly Glu
465                 470                 475                 480

Asp Lys Thr Arg Gly Asp Lys Val Asn Val Thr Pro Ile Asn Ser Tyr
                485                 490                 495

Ile Lys Glu Ile Phe Asn Ile Val Asp Val Val Gly Leu Asn Tyr Ser
            500                 505                 510

Glu Asn Asn Tyr Asp Gly Tyr His Lys Gln Asn Pro Ser Trp Lys Leu
        515                 520                 525

Tyr Gly Ser Glu Thr Ser Ser Ala Thr Arg Ser Arg Gly Val Tyr Thr
    530                 535                 540

His Pro Tyr Gln Tyr Asn Gln Ser Thr Lys Tyr Ala Asp Leu Gln Gln
545                 550                 555                 560

Ser Ser Tyr Asp Asn Asp Tyr Val Gly Trp Gly Arg Thr Ala Glu Asp
                565                 570                 575

Ala Trp Lys Tyr Asp Arg Asp Leu Lys His Ile Ala Gly Gln Phe Ile
            580                 585                 590

Trp Thr Gly Phe Asp Tyr Ile Gly Glu Pro Thr Pro Tyr Tyr Asn Ser
        595                 600                 605

Tyr Pro Ala Lys Ser Ser Tyr Phe Gly Ala Val Asp Thr Ala Gly Phe
    610                 615                 620

Pro Lys Asp Ile Phe Tyr Tyr Gln Ser Gln Trp Lys Lys Glu Pro
625                 630                 635                 640

Met Val His Leu Leu Pro His Trp Asn Trp Lys Glu Gly Glu Lys Val
                645                 650                 655

Arg Val Leu Ala Tyr Thr Asn Ala Ser Lys Val Glu Leu Val Leu Asn
            660                 665                 670

Gly Glu Ser Leu Gly Glu Lys Asn Tyr Asp Asn Lys Gln Thr Ser Trp
        675                 680                 685

Gly Ala Pro Tyr Lys Glu Thr Lys Asp Gly Lys Thr Tyr Leu Glu Trp
    690                 695                 700

Ala Val Pro Phe Lys Pro Gly Lys Leu Glu Ala Val Ala Lys Asp Glu
```

```
                705                 710                 715                 720
Asn Gly Lys Val Ile Ala Arg Asp Gln Val Val Thr Ala Gly Glu Pro
            725                 730                 735

Ala Ser Val Arg Leu Thr Ala Asp Arg Lys Val Val Lys Ala Asp Gly
            740                 745                 750

Thr Asp Leu Ser Phe Ile Thr Ala Asp Ile Val Asp Ser Lys Gly Ile
            755                 760                 765

Val Val Pro Asp Ala Asp His Leu Ile Thr Phe Asn Val Thr Gly Gln
            770                 775                 780

Gly Glu Leu Ala Gly Val Asp Asn Gly Asn Ala Ser Ser Val Glu Arg
785                 790                 795                 800

Tyr Lys Asp Asn Lys Arg Lys Ala Phe Ser Gly Lys Ala Leu Ala Ile
            805                 810                 815

Val Gln Ser Ser Lys Leu Ser Gly Lys Ile Thr Val His Ala Ser Val
            820                 825                 830

Pro Gly Leu Ser Ser Asp Ser Thr Ser Val Phe Thr Val Thr Pro
            835                 840                 845
```

<210> SEQ ID NO 15
<211> LENGTH: 847
<212> TYPE: PRT
<213> ORGANISM: Artificial Sequence
<220> FEATURE:
<223> OTHER INFORMATION: Modified enzyme

<400> SEQUENCE: 15

```
Met Lys Lys Ala Ile Ser Cys Val Phe Leu Ile Ser Ala Leu Ile Leu
1               5                   10                  15

Ser Ser Phe Gln Val Pro Val Gln Gly Gln Ala Met Ser Lys Thr Thr
            20                  25                  30

Ser Ala Ala Gly Asn Ser Val Ser Tyr Asp Gly Glu Arg Arg Val Asn
            35                  40                  45

Phe Asn Glu Asn Trp Arg Phe Gln Arg Glu Thr Asn Gly Ser Ile Ala
            50                  55                  60

Gly Ala Gln Asn Pro Gly Phe Asp Asp Ser Ser Trp Arg Lys Leu Asn
65                  70                  75                  80

Leu Pro His Asp Trp Ser Ile Glu Leu Asp Phe Asn Lys Asn Ser Leu
                85                  90                  95

Ala Thr His Glu Gly Gly Tyr Leu Asp Gly Ile Gly Trp Tyr Arg
                100                 105                 110

Lys Thr Phe Thr Ile Pro Glu Ser Met Lys Gly Lys Arg Ile Ser Leu
            115                 120                 125

Asp Phe Asp Gly Val Tyr Met Asn Ser Thr Thr Tyr Leu Asn Gly Glu
            130                 135                 140

Val Leu Gly Thr Tyr Pro Phe Gly Tyr Asn Ala Phe Ser Tyr Asp Ile
145                 150                 155                 160

Ser Asp Lys Leu Tyr Pro Asp Gly Arg Ala Asn Val Leu Val Val Lys
                165                 170                 175

Val Asn Asn Thr Gln Pro Ser Ser Arg Trp Tyr Ser Gly Ser Gly Ile
            180                 185                 190

Tyr Arg Asn Val Tyr Leu Thr Val Thr Asp Pro Ile His Val Ala Arg
                195                 200                 205

Tyr Gly Thr Phe Val Thr Thr Pro Asn Leu Glu Lys Ser Ile Lys Glu
            210                 215                 220

Asp Arg Ala Asp Val Asn Ile Lys Thr Lys Ile Ser Asn Asp Ala Ala
```

```
            225                 230                 235                 240
    Glu Ala Lys Gln Val Lys Ile Lys Ser Thr Ile Tyr Asp Gly Ala Gly
                        245                 250                 255

Asn Thr Val Gln Thr Val Glu Thr Glu Lys Thr Ala Ala Ala Gly
                260                 265                 270

Thr Val Thr Pro Phe Glu Gln Asn Thr Val Ile Lys Gln Pro Lys Leu
                        275                 280                 285

Trp Ser Ile Asp Lys Pro Tyr Arg Tyr Asn Leu Val Thr Glu Val Ile
            290                 295                 300

Val Gly Pro Gln Thr Val Asp Thr Tyr Glu Thr Lys Phe Gly Val Arg
    305                 310                 315                 320

Tyr Phe Lys Phe Asp Glu Asn Glu Gly Phe Ser Leu Asn Gly Glu Tyr
                        325                 330                 335

Met Lys Leu His Gly Val Ser Met His His Asp Leu Gly Ala Leu Gly
                340                 345                 350

Ala Ala Thr Asn Ala Arg Gly Val Glu Arg Gln Met Gln Ile Met Lys
                355                 360                 365

Asp Met Gly Val Asn Ala Ile Arg Val Thr His Asn Pro Ala Ser Pro
    370                 375                 380

Glu Leu Leu Glu Ala Ala Asn Lys Leu Gly Leu Phe Ile Ile Glu Glu
    385                 390                 395                 400

Ala Phe Asp Ser Trp Ala Gln Ser Lys Lys Pro Tyr Asp Tyr Gly Arg
                        405                 410                 415

Phe Phe Asn Ala Trp Ala Glu His Asp Ile Lys Glu Met Val Asp Arg
                        420                 425                 430

Gly Lys Asn Glu Pro Ala Ile Ile Met Trp Ser Ile Gly Asn Glu Ile
                435                 440                 445

Tyr Asp Thr Thr Asn Ala Ala Gly Val Glu Thr Ala Arg Asn Leu Val
                450                 455                 460

Gly Trp Val Lys Glu Ile Asp Thr Thr Arg Pro Thr Thr Ile Gly Glu
    465                 470                 475                 480

Asp Lys Thr Arg Gly Asp Lys Val Asn Val Thr Pro Ile Asn Ser Tyr
                        485                 490                 495

Ile Lys Glu Ile Phe Asn Ile Val Asp Val Val Gly Leu Asn Tyr Ser
                        500                 505                 510

Glu Asn Asn Tyr Asp Gly Tyr His Lys Gln Asn Pro Ser Trp Lys Leu
                515                 520                 525

Tyr Gly Ser Glu Thr Ser Ser Ala Thr Arg Ser Arg Gly Val Tyr Thr
                530                 535                 540

His Pro Tyr Gln Tyr Asn Gln Ser Thr Lys Tyr Ala Asp Leu Gln Gln
    545                 550                 555                 560

Ser Ser Tyr Asp Asn Asp Tyr Val Gly Trp Gly Arg Thr Ala Glu Asp
                        565                 570                 575

Ala Trp Lys Tyr Asp Arg Asp Leu Lys His Ile Ala Gly Gln Phe Ile
                        580                 585                 590

Trp Thr Gly Phe Asp Tyr Ile Gly Glu Pro Thr Pro Tyr Tyr Asn Ser
                595                 600                 605

Tyr Pro Ala Lys Ser Ser Tyr Phe Gly Ala Val Asp Thr Ala Gly Phe
                610                 615                 620

Pro Lys Asp Ile Phe Tyr Tyr Gln Ser Gln Trp Lys Lys Glu Pro
    625                 630                 635                 640

Met Val His Leu Leu Pro His Trp Asn Trp Lys Glu Gly Glu Lys Val
                        645                 650                 655
```

-continued

```
Arg Val Leu Ala Tyr Thr Asn Ala Ser Lys Val Glu Leu Val Leu Asn
            660             665             670
Gly Glu Ser Leu Gly Glu Lys Asn Tyr Asp Asn Lys Gln Thr Ser Trp
        675             680             685
Gly Ala Pro Tyr Lys Glu Thr Lys Asp Gly Lys Thr Tyr Leu Glu Trp
        690             695             700
Ala Val Pro Phe Lys Pro Gly Lys Leu Glu Ala Val Ala Lys Asp Glu
705             710             715             720
Asn Gly Lys Val Ile Ala Arg Asp Gln Val Val Thr Ala Gly Glu Pro
                725             730             735
Ala Ser Val Arg Leu Thr Ala Asp Arg Lys Val Val Lys Ala Asp Gly
                740             745             750
Thr Asp Leu Ser Phe Ile Thr Ala Asp Ile Val Asp Ser Lys Gly Ile
        755             760             765
Val Val Pro Asp Ala Asp His Leu Ile Thr Phe Asn Val Thr Gly Gln
    770             775             780
Gly Glu Leu Ala Gly Val Asp Asn Gly Asn Ala Ser Ser Val Glu Arg
785             790             795             800
Tyr Lys Asp Asn Lys Arg Lys Ala Phe Ser Gly Lys Ala Leu Ala Ile
            805             810             815
Val Gln Ser Ser Lys Leu Ser Gly Lys Ile Thr Val His Ala Ser Val
            820             825             830
Pro Gly Leu Ser Ser Asp Ser Thr Ser Val Phe Thr Val Thr Pro
            835             840             845
```

MODIFIED β-GALACTOSIDASE

TECHNICAL FIELD

The present invention relates to a β-galactosidase. Specifically, the present invention relates to modifications of a β-galactosidase derived from *Bacillus circulans*, uses of modified enzymes thereof, and others. The present application claims priority to Japanese Patent Application No. 2014-166897, filed on Aug. 19, 2014, the entire content of which is incorporated herein by reference.

BACKGROUND ART

β-galactosidase (EC 3.2.1.23) is an enzyme which hydrolyzes a β-D-galactoside linkage to release D-galactose, and β-galactosidase isozymes are generally found in a wide range of microorganisms and plants. β-galactosidase is otherwise referred to as lactase. β-galactosidase is also capable of transferring a galactoside linkage, and there are known methods in which this capability is used to produce galacto-oligosaccharides (oligosaccharides having galactose residues).

Various β-galactosidases are known to be produced by a koji mold *Aspergillus oryzae*, yeasts *Kluyveromyces lactis* and *Kluyveromyces marxinus*, a bacterium *Bacillus circulans*, and others. Among β-galactosidase enzymes produced by these microorganisms, the β-galactosidase derived from *Bacillus circulans* (see Patent Literature 1 and Non Patent Literature 1) is an enzyme allowing the production of galacto-oligosaccharides from lactose, and is an important enzyme in the industrial production of galacto-oligosaccharides (for example, a preparation of β-galactosidase isozymes is marketed under a trade name of "BIOLACTA").

CITATIONS LIST

Patent Literature

Patent Literature 1: WO 2010/140435

Non Patent Literatures

Non Patent Literature 1: Song, J., Abe, K., Imanaka, H., Imamura, K., Minoda, M., Yamaguchi, S., & Nakanishi, K. (2010). Causes of the production of multiple forms of β-galactosidase by *Bacillus circulans*. Bioscience, biotechnology, and biochemistry, 75(2), 268-278.

SUMMARY OF THE INVENTION

Problems to be Solved by the Invention

Enzymatic production of oligosaccharides is generally carried out with heating a reaction mixture after the addition of the enzyme to a solution of a substrate which is a saccharide such as lactose. In this enzymatic reaction, it is desirable that for example, in order to increase the solubility of the substrate or to avoid bacterial contamination, the reaction temperature is as high as possible. It is known that enzymatic transglycosylation reactions generally proceed efficiently with a higher substrate concentration. In addition, higher reaction temperatures result in an increased solubility of the substrate, thereby making it possible to increase the substrate concentration. For this reason, an improvement in the heat resistance of a transglycosylating enzyme is desired particularly for industrial production of oligosaccharides. In this connection, it has been reported that modifications of an enzyme, for example, by an enzyme engineering technique lead to a decrease in the stability of the enzyme. While improvements in enzyme properties has been achieved by enzyme modifications, the enzyme may have impaired stability, such as heat resistance, so that it is not put to practical use. In this case, if additional modifications can be made to improve its stability, then a great advance will be made toward its practical use.

Therefore, the present invention has a purpose of providing a technique for enhancing the heat resistance of a β-galactosidase useful, for example, in the production of oligosaccharides, products resulting therefrom, applications thereof, and others.

Means for Solving the Problems

From previous investigations, it is known that the β-galactosidase produced by *Bacillus circulans* is comprised of four enzymes with different molecular weights, that is, β-galactosidase enzymes with a molecular weight of 195 kD (BgaD-A, SEQ ID NO: 1), 160 kD (BgaD-B, SEQ ID NO: 2), 135 kD (BgaD-C, SEQ ID NO: 3), and 86 kD (BgaD-D, SEQ ID NO: 4). Among these enzymes, BgaD-D is an enzymatically active β-galactosidase enzyme having the smallest size, and exhibits the highest activity of transglycosylation. These enzyme properties make BgaD-D particularly useful for the production of oligosaccharides. Paying attention to this regard, the inventors undertook the identification of the steric structure of BgaD-D. Specifically, the inventors employed a hanging-drop vapor-diffusion method in which as precipitating agent, use was made of 0.4 M sodium citrate tribasic dihydrate, 1.0 M sodium acetate trihydrate (pH 4.0), and 25% w/v Polyethylene glycol 3,350, and used highly purified BgaD-D to make attempts at its crystallization. While about one year was required, the inventors succeeded in the observation of only three crystals having been yielded near the interface to the heterogeneous solution. From among these three crystals, selection of a crystal was made to attempt to mount it on an apparatus for crystal structure analysis. In the result, one crystal led to the success in collecting its reflection data. Then, this data was used for a calculation using a phase determination software, which required about two weeks. In the result, the steric structure of BgaD-D was fortunately successfully identified. Subsequently, on the basis of its steric structural information, attempts were made to identify amino acids that were expected to be effective for making the BgaD-D enzyme more heat-resistant, which amino acids were then subjected to mutation. From results of a detailed investigation of properties of mutated variants, three mutation sites were found to be effective for making the enzyme more heat-resistant. Results of further investigation revealed that combinations of effective mutations introduced at these sites brought about a further improvement in the heat resistance. The inventions described below are based mainly on the above-described results and on their considerations.

[1] A β-galactosidase comprising an amino acid sequence which is different from a reference β-galactosidase amino acid sequence in that one or more amino acids selected from the group consisting of the following (1) to (3) is/are proline, wherein the reference β-galactosidase amino acid sequence shows a 90% or more identity to the amino acid sequence of SEQ ID NO: 4:

(1) an amino acid corresponding to lysine at position 166 of the amino acid sequence of SEQ ID NO: 4;

(2) an amino acid corresponding to glycine at position 307 of the amino acid sequence of SEQ ID NO: 4; and (3) an amino acid corresponding to alanine at position 833 of the amino acid sequence of SEQ ID NO: 4.

[2] The β-galactosidase according to [1], wherein the enzyme exhibits improved heat resistance relative to that of the reference β-galactosidase.

[3] The β-galactosidase according to [1] or [2], wherein the amino acids (1) and (2), the amino acids (1) and (3), or the amino acids (1) to (3) have been subjected to the substitution.

[4] The β-galactosidase according to any one of [1] to [3], wherein the reference β-galactosidase consists of the amino acid sequence of SEQ ID NO: 4.

[5] The β-galactosidase according to [1], consisting of the amino acid sequence of any one of SEQ ID NOs: 9 to 15.

[6] A β-galactosidase comprising an amino acid sequence which is different from a reference β-galactosidase amino acid sequence in that one or more amino acids selected from the group consisting of the following (1) to (3) is/are proline, wherein the reference β-galactosidase amino acid sequence shows a 90% or more identity to the amino acid sequence of any one of SEQ ID NOs: 1 to 3:

(1) an amino acid corresponding to lysine at position 166 of the amino acid sequence of SEQ ID NO: 4;

(2) an amino acid corresponding to glycine at position 307 of the amino acid sequence of SEQ ID NO: 4; and (3) an amino acid corresponding to alanine at position 833 of the amino acid sequence of SEQ ID NO: 4.

[7] A gene encoding the β-galactosidase according to any one of [1] to [6].

[8] A recombinant DNA comprising the gene according to [7].

[9] A microorganism carrying the recombinant DNA according to [8].

[10] An enzyme agent comprising the β-galactosidase according to any one of [1] to [6].

[11] A method for producing an oligosaccharide, characterized in that the β-galactosidase according to any one of [1] to [6] is subjected to a reaction with a disaccharide, oligosaccharide, or polysaccharide having at least one of β-1,3-, β-1,4-, and β-1,6-linkages.

[12] A method for designing a β-galactosidase, comprising:

(i) a step of identifying, in a reference β-galactosidase amino acid sequence which shows a 90% or more identity to the amino acid sequence of any one of SEQ ID NOs: 1 to 4, one or more amino acids selected from the group consisting of the following (1) to (3):

(1) an amino acid corresponding to lysine at position 166 of the amino acid sequence of SEQ ID NO: 4;

(2) an amino acid corresponding to glycine at position 307 of the amino acid sequence of SEQ ID NO: 4; and (3) an amino acid corresponding to alanine at position 833 of the amino acid sequence of SEQ ID NO: 4;

(ii) a step of constructing, on the basis of the reference β-galactosidase amino acid sequence, an amino acid sequence in which proline has been substituted for the amino acid(s) identified in step (i).

[13] The designing method according to [12], wherein the reference β-galactosidase consists of the amino acid sequence of SEQ ID NO: 4.

[14] A method for preparing a β-galactosidase, comprising:

(I) a step of providing a nucleic acid coding the amino acid sequence of any one of SEQ ID NOs: 9 to 15 or the amino acid sequence constructed by the designing method of [12] or [13];

(II) a step of expressing the nucleic acid; and (III) a step of collecting the expression product.

BRIEF DESCRIPTION OF THE DRAWINGS

FIG. 2: Results of an analysis of protein denaturation temperature with a circular dichroism spectropolarimeter (for single mutation variants).

FIG. 3: Results of an analysis of protein denaturation temperature with a circular dichroism spectropolarimeter (for multiple mutation variants).

DETAILED DESCRIPTION OF THE INVENTION

Figure 1:
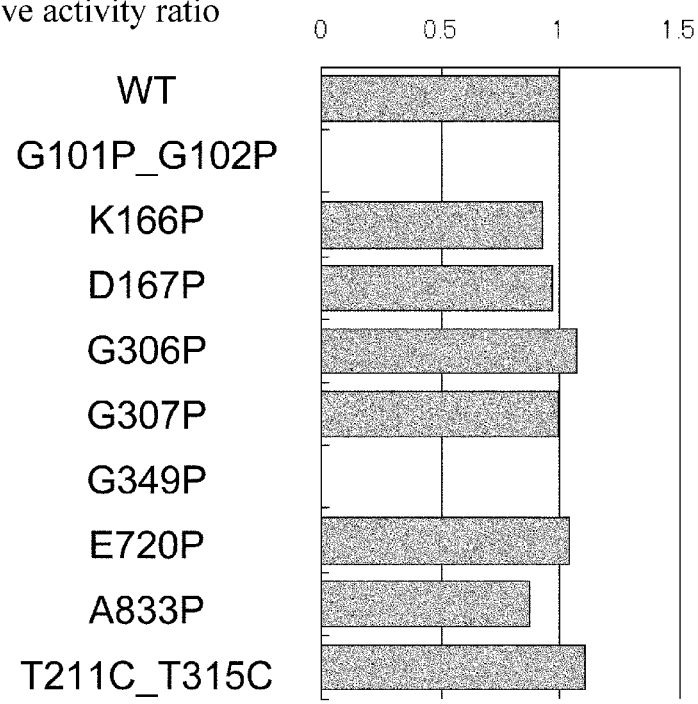
FIG. 1: Enzyme activities of various variants. (A) Activities measured at 40° C. and 60° C. (B) Activity ratios (activity measurements at 60° C. to those measured at 40° C.).

For convenience of description, some of the terms used in relation to the present invention are defined as follows.

Terminology

The term "modified β-galactosidase" refers to an enzyme obtained by modification or mutation of a particular β-galactosidase (which is referred to as a "reference β-galactosidase" for convenience of description). The reference β-galactosidase is a β-galactosidase produced by *Bacillus circulans*. From previous investigations, it is known that the β-galactosidase from *Bacillus circulans* is comprised of four enzymes with different molecular weights, that is, β-galactosidase enzymes with a molecular weight of 195 kD (also referred to as BgaD-A), 160 kD (also referred to as BgaD-B), 135 kD (also referred to as BgaD-C), and 86 kD (also referred to as BgaD-D). In the present invention, any one of these four enzymes will be used as a reference β-galactosidase. Therefore, the reference β-galactosidase typically has any one of the amino acid sequences of BgaD-A (SEQ ID NO: 1), BgaD-B (SEQ ID NO: 2), BgaD-C(SEQ ID NO: 3), and BgaD-D (SEQ ID NO: 4), while it is also possible that, as a reference β-galactosidase, to use an enzyme whose amino acid sequence shows a 90% or more identity to that of any one of SEQ ID NOs: 1 to 4, as long as the enzyme exhibits β-galactosidase activity. Preferably, as a reference β-galactosidase, an enzyme whose amino acid sequence shows a 95% or more identity, more preferably a 98% or more identity, most preferably a 99% or more identity to that of any one of SEQ ID NOs: 1 to 4, as long as the enzyme exhibits β-galactosidase activity. In this connection, the base sequences encoding BgaD-A, BgaD-B, BgaD-C, and BgaD-D are represented in SEQ ID NOs: 5, 6, 7, and 8, respectively.

Among these four enzymes, BgaD-D exhibits the highest transglycosylation activity, and is particularly useful for the production of oligosaccharides. In a most preferable embodiment of the present invention, the reference β-galactosidase is a β-galactosidase consisting of the amino acid sequence of BgaD-D (SEQ ID NO: 4).

In the present invention, an "amino acid substitution" is carried out as modification or mutation. Therefore, some amino acid residues are found to be different when a modified β-galactosidase and a reference β-galactosidase therefor are compared. In the specification, a modified β-galactosidase is also referred to as a modified enzyme, an variant β-galactosidase, a variant, or others.

In the specification, amino acids are designated according to the common practice, as their single letters as described below:

methionine: M; serine: S; alanine: A; threonine: T; valine: V; tyrosine: Y; leucine: L; asparagine: N; isoleucine: I; glutamine: Q; proline: P; aspartic acid: D; phenylalanine: F; glutamic acid: E; tryptophan: W; lysine: K; cysteine: C; arginine: R; glycine: G; and histidine: H.

In addition, an amino acid residue at a mutation site (an amino acid residue to be substituted with another amino acid) is expressed in a combination of the above-described single letter representing the kind of the amino acid residue and the figure representing the position of the amino acid residue. For example, if lysine at position 166 is a mutation site, then the amino acid is designated as "K166."

(Modified β-Galactosidases)

A first aspect of the present invention is directed to a modified β-galactosidase (modified enzyme). The modified enzyme of the present invention has an amino acid sequence which is different from a reference β-galactosidase amino acid sequence in that a proline substitution at the position(s) of one or more amino acids selected from the group consisting of the following (1) to (3) has been made, wherein the reference β-galactosidase amino acid sequence shows a 90% or more identity to the amino acid sequence of SEQ ID NO. 4:

(1) an amino acid corresponding to lysine at position 166 of the amino acid sequence of SEQ ID NO. 4;

(2) an amino acid corresponding to glycine at position 307 of the amino acid sequence of SEQ ID NO. 4; and (3) an amino acid corresponding to alanine at position 833 of the amino acid sequence of SEQ ID NO. 4.

As demonstrated in Examples described below, the amino acid residues that are selected as a mutation site are ones that are among amino acid residues identified based on the steric structure of BgaD-D (SEQ ID NO: 4) which have been found to be effective in improving the heat resistance of the enzyme by detailed investigations. In the present invention, these amino acid residues are selected as a target for mutation and modified, thereby to achieve an improvement in the heat resistance of the enzyme.

The reference β-galactosidase has a 90% or more identical amino acid sequence, preferably a 95% or more identical amino acid sequence, more preferably a 98% or more identical amino acid sequence, most preferably a 99% or more identical amino acid sequence, relative to the amino acid sequence of any one of SEQ ID NOs: 1 to 4. In these reference β-galactosidases, a reference β-galactosidase other than that having the same amino acid sequence as that of SEQ ID NO: 4 can be different in the position number of an amino acid residue to be substituted (the position of an amino acid residue to be substituted in the sequence of the reference β-galactosidase), for example, due to amino acid insertion or deletion. Taking this into account, the present invention uses the expression "amino acid corresponding to" as an expression for specifying an amino acid that is to be substituted. Here, the term "corresponding" means that between proteins (enzymes) that are compared, a comparable contribution is made in exerting their function. For example, when an amino acid sequence to be compared is aligned with a reference amino acid sequence (that is, the amino acid sequence of SEQ ID NO: 4), taking into account a partial homology between their primary structures (amino acid sequences), so as to allow their optimal comparison (in this case, the alignment may be optimized by inserting gaps, as appropriate), then the amino acid in the amino acid sequence to be compared that is located at the position corresponding to a given amino acid in the reference amino acid sequence can be specified as an "amino acid corresponding to" the given amino acid. Instead of or in addition to a comparison of proteins (enzymes) in their primary structures, a comparison in their steric structures (three-dimensional structures) also allows one to specify an "amino acid corresponding to" a given amino acid. The use of the steric structural information brings about comparison results of high reliability. In this case, it is possible to adopt procedures in which the alignment of two or more enzymes is made while comparing their atomic coordinates in the steric structures. When BgaD-A, BgaD-B, BgaD-C, and BgaD-D are used as a reference β-galactosidase, an "amino acid corresponding to" a given amino acid of the reference β-galactosidase is as follows:

(1) An amino acid corresponding to K166 of the amino acid sequence of SEQ ID NO: 4 is
  K166 in the case of BgaD-A,
  K166 in the case of BgaD-B,
  K166 in the case of BgaD-C, and
  K166 in the case of BgaD-D.

(2) An amino acid corresponding to G307 of the amino acid sequence of SEQ ID NO: 4 is
  G307 in the case of BgaD-A,
  G307 in the case of BgaD-B,
  G307 in the case of BgaD-C, and
  G307 in the case of BgaD-D.

(3) An amino acid corresponding to A833 of the amino acid sequence of SEQ ID NO: 4 is
  A833 in the case of BgaD-A,
  A833 in the case of BgaD-B,
  A833 in the case of BgaD-C, and
  A833 in the case of BgaD-D.

As explained in the following Examples described below, each of the amino acids (1) to (3) that are to be substituted is a component of a β-turn. In the present invention, proline is substituted for at least one of these amino acids, whereby the structure of the enzyme is stabilized and an improvement in its heat resistance is achieved. Proline forms a unique peptide bond of (=N—CO—) by intermolecular dehydration between the H atom at the imino (=NH) group of proline and the carboxylic group of another amino acid. In this type of peptide bond, the N atom possesses no hydrogen atom, and is incapable of hydrogen bonding. In addition, since proline is an amino acid having a cyclic structure, the bond angles within the proline molecule are fixed, resulting in the stabilization of the steric structure of the protein. The proline that is an amino acid after substitution may have a modification, as long as the substitution brings about a characteristic action by which such a structural stabilization is achieved. In this context, examples of such a modification can be hydroxylation, acetylhydroxyproline.

As supported by Examples described below, combinations of modifications of the amino acids (1) to (3) that are to be substituted, i.e., combined modifications of these amino acids lead to an additional improvement in the heat resistance of the enzyme. Accordingly, in a preferable embodiment of a modified enzyme of the present invention, proline has been substituted for two of these amino acids (1) to (3), and in a more preferable embodiment, for all these amino acids (1) to (3). In this context, because the proline substitution for the amino acid (1) has been found to be particularly useful (see Examples), a combination of the amino acids (1) and (2) or the amino acids (1) and (3) may be selected when proline is substituted for two of the amino acids (1) to (3).

Examples of the amino acid sequences of modified enzymes of the present invention are represented in SEQ ID NOs: 9 to 15. These sequences are amino acid sequences of modified enzymes obtained by proline substitution for one amino acid of the above-described amino acids, two amino acids (the amino acids (1) and (2), (1) and (3), or (2) and (3)), or three amino acids (the amino acids (1), (2), and (3)) in BgaD-D. The correspondence relationship between SEQ ID NOs: and amino acid substitutions is as follows:

|   | Amino acid sequence: | Amino acid substitution |
|---|---|---|
| A. | SEQ ID NO: 9: | K166P |
| B. | SEQ ID NO: 10: | G307P |
| C. | SEQ ID NO: 11: | A833P |
| D. | SEQ ID NO: 12: | K166P and G307P |
| E. | SEQ ID NO: 13: | K166P and A833P |
| F. | SEQ ID NO: 14: | G307P and A833P |
| G. | SEQ ID NO: 15: | K166P, G307P, and A833P |

In general, when a portion of the amino acid sequence of a given protein has been subjected to mutagenesis, a mutated version of the protein may have a function equivalent to that of the original unmutated protein. That is, it is sometimes observed that a mutation in a given amino acid sequence does not lead to substantial effects on a protein's function, whereby the function is maintained between before and after the mutation is introduced. Taking this common general technical knowledge into account, it can be considered that when compared to an above-described modified enzyme consisting of an amino acid sequence in which proline has been substituted for one or more amino acids selected from the group consisting of the above-described amino acids (1) to (3), a modified enzyme which has a slight difference in the amino acid sequence (wherein such a difference in the amino acid sequence is located in a position(s) other than the position at which the above-described amino acid substitution has been performed), but which nevertheless does not have substantial differences in properties is an enzyme that is substantially the same as the above-described modified enzyme. The "slight difference in the amino acid sequence" in this context typically refers to the occurrence of a mutation(s) (change(s)) in the amino acid sequence resulting from deletion or substitution of one to several amino acids (for example, up to three, five, seven, or ten amino acids) contained in the amino acid sequence, or addition or insertion of one to several amino acids (for example, up to three, five, seven, or ten amino acids), or combinations thereof. The identity (%) between the amino acid sequences of an "enzyme that is substantially the same" and an above-described modified enzyme that is used as the reference is, for example, 90% or more, preferably 95% or more, more preferably 98% or more, most preferably 99% or more. In this context, differences in the amino acid sequence may occur at two or more positions. A "slight difference in the amino acid sequence" preferably results from conservative amino acid substitution.

Incidentally, a β-galactosidase derived from *Bacillus circulans* is described in WO 2010/098561. It is also possible that into this β-galactosidase, a mutation is introduced which corresponds to any of the amino acid substitutions disclosed in the present specification, thereby resulting in the generation of a modified β-galactosidase e. In this regard, the sequence encoding the β-galactosidase disclosed in WO 2010/098561 shows about 70% identity to that encoding a reference β-galactosidase in the present application (SEQ ID NO: 5).

(Nucleic Acid Coding for Modified β-Galactosidase, Etc.)

The second aspect of the present invention provides a nucleic acid relating to the modified enzyme of the invention. That is, provided are a gene coding for the modified enzyme, a nucleic acid that can be used as a probe for identifying a nucleic acid coding for the modified enzyme, and a nucleic acid that can be used as a primer for amplifying or mutating a nucleic acid coding for the modified enzyme.

The gene coding for a modified enzyme is typically used in preparation of the modified enzyme. According to a genetic engineering procedure using the gene coding for a modified enzyme, a modified enzyme in a more homogeneous state can be obtained. Further, the method can be a preferable method also in the case of preparing a large amount of a modified enzyme. Note that uses of the gene coding for a modified enzyme are not limited to preparation of a modified enzyme. For example, the nucleic acid can also be used as a tool for an experiment intended for clarification of action mechanisms of a modified enzyme or a tool for designing or preparing a further modified form of an enzyme.

The "gene coding for a modified enzyme" herein refers to a nucleic acid capable of obtaining the modified enzyme when it is expressed, and includes, as a matter of course of a nucleic acid having a base sequence corresponding to the amino acid sequence of the modified enzyme, also a nucleic acid obtained by adding a sequence that does not code for an amino acid sequence to such a nucleic acid. Degeneracy of a codon is also considered.

The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a base sequence in a part (hereinafter also referred to as a "homologous nucleic acid", and a base sequence defining a homologous nucleic acid is also referred to as a "homologous base sequence") as compared to the base sequence of the gene coding for the modified enzyme of the invention, although functions of a protein coded by the nucleic acid are equal. An example of the homologous nucleic acid includes a DNA composed of a base sequence containing substitution, deletion, insertion, addition or inversion of 1 to several nucleotides on the basis of the base sequence of the nucleic acid coding for the modified enzyme of the present invention and coding for a protein having enzyme activity characteristic to the modified enzyme. Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having the complementary base sequence to the base sequence of the gene coding for the modified enzyme of the invention. Another embodiment of the present invention provides a nucleic acid having a base sequence with an identity of at least about 60%, 70%, 80%, 90%, 95%, 99%, or 99.9% to the base sequence of the gene coding for the modified enzyme of the invention or the complementary base sequence Another embodiment of the present invention relates to a nucleic acid having a base sequence hybridizing to the complementary base sequence to the base sequence of the gene coding for the modified enzyme of the invention or its homologous base sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 µg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 µg/ml of modified salmon sperm DNA, and a 50 mM phosphate buffer (pH 7.5) as a hybridization liquid.

Another embodiment of the present invention provides a nucleic acid (nucleic acid fragment) having a part of the base sequence of the gene coding for the modified enzyme of the invention or the complementary base sequence. Such a nucleic acid fragment can be used in detection, identification, and/or amplification of a nucleic acid having the base sequence of the gene coding for the modified enzyme of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the base sequence of the gene coding for the modified enzyme of the present invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a modified enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a modified enzyme can be used. Examples of *Escherichia coli* include *Escherichia coli* BL21 (DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Felgner, P. L. et al., Proc. Natl. Acad. Sci. U.S.A. 84, 7413-7417 (1984)). Note that the microorganism of the present invention can be used in producing the modified enzyme of the present invention.

(Enzyme Agent Containing Modified β-Galactosidase)

The modified enzyme of the present invention is provided, for example, in the form of an enzyme agent. The enzyme agent may contain an excipient, a buffer agent, a suspending agent, a stabilizer, a preservative, an antiseptic, saline and the like besides the active ingredient (the modified enzyme of the present invention). As the excipient, starch, dextrin, maltose, trehalose, lactose, D-glucose, sorbitol, D-mannitol, white soft sugar, glycerol and the like can be used. As the buffer agent, phosphates, citrates, acetates and the like can be used. As the stabilizer, propylene glycol, ascorbic acid and the like can be used. As the preservative, phenol, benzalkonium chloride, benzyl alcohol, chlorobutanol, methylparaben and the like can be used. As the antiseptic, ethanol, benzalkonium chloride, paraoxybenzoic acid, chlorobutanol and the like can be used.

(Applications of Modified β-Galactosidases)

A further aspect of the present invention provides applications of modified enzymes or enzyme preparations. Examples of these applications include use for production of galacto-oligosaccharides, production and processing of pharmaceutical products and supplements for lactose-intolerant patients, production and processing of dairy products (for example, processed milk products such as lactose-reduced milk, powdered milk such as skim milk and nursing powdered milk, yogurts, and others), and production and processing of medical foods.

A modified enzyme of the present invention is particularly useful for the production of galacto-oligosaccharides. In the production of galacto-oligosaccharides, for example, to a pre-heated solution in which lactose has been dissolved (for example, 30% to 50% lactose, pH 7.0) is added a modified enzyme of the present invention in a predetermined amount (for example, 50 to 1000 U), and the mixture is left to stand at about 58° C. for a period of 1 to 10 hours, thereby to produce galacto-oligosaccharides. Since the modified enzyme of the present invention has improved heat resistance, the reaction can be performed at relatively higher temperatures, thereby resulting in an increase in their production efficiency. In this context, the galacto-oligosaccharide is represented by Gal-(Gal)n-Glc, wherein n is 0 to 5 or so, and Gal is a galactose residue and Glc is a glucose residue. The type of linkage between sugar residues includes β1-6, β1-3, β1-4, and β1-2, and besides these, α1-3, α1-6, and others.

A modified enzyme and the parent wild-type enzyme thereof are different in their properties. Therefore, the use of a modified enzyme and the parent wild-type enzyme thereof in combination makes it possible to manufacture a galacto-oligosaccharide of which the production cannot be achieved (or is not suitable) by using the wild-type enzyme alone. When a plurality of modified enzymes with different properties and the parent wild-type enzyme thereof are used in combination, it would be possible to further increase the kind of galacto-oligosaccharides to be produced. Thus, the use of (one or more) modified enzymes and the parent wild-type enzyme thereof in combination is also effective in producing various galacto-oligosaccharides separately as intended.

Methods by which galacto-oligosaccharides (a mixture of various types of galacto-oligosaccharides) are obtained using a plurality of modified enzymes (a combination of a plurality of modified enzymes, or alternatively a combination of a given wild-type enzyme and one or more modified enzymes thereof) include, when classified roughly, one in which galacto-oligosaccharides that have been produced using respective enzymes are mixed, one in which a plurality of enzymes is allowed to act on a raw material (lactose) at the same time, and one in which a plurality of enzymes is allowed to act on a raw material in a stepwise manner.

(Method for Designing Modified β-Galactosidases)

A further aspect of the present invention is directed to a method for designing a modified enzyme. In the designing method of the present invention, steps (i) and (ii) described below are carried out.

Step (i), which is a step of identifying, in a reference β-galactosidase amino acid sequence which shows a 90% or more identity to the amino acid sequence of any one of SEQ ID NOs: 1 to 4, one or more amino acids selected from the group consisting of the following (1) to (3):

(1) an amino acid corresponding to lysine at position 166 of the amino acid sequence of SEQ ID NO: 4;
(2) an amino acid corresponding to glycine at position 307 of the amino acid sequence of SEQ ID NO: 4; and
(3) an amino acid corresponding to alanine at position 833 of the amino acid sequence of SEQ ID NO: 4.

The amino acids (1) to (3) that are to be substituted have been identified as amino acids that are effective for improving the heat resistance of β-galactosidase. In the designing method of the present invention, proline is substituted for these amino acids, whereby an improvement in the heat resistance of β-galactosidase is achieved.

The target for mutation in the designing method of the present invention is a β-galactosidase. An enzyme that is to be mutated is typically a wild-type enzyme (an enzyme found in nature). However, the present invention does not exclude, as an enzyme that is to be mutated, an enzyme into which some mutation or modification has already been introduced. An enzyme that is to be mutated has an amino acid sequence that is 90% or more identical to that of any one of SEQ ID NOs: 1 to 4. In this context, such an amino acid sequence preferably has a sequence identity of 95% or more, more preferably 98% or more, and most preferably 99% or more.

In the present invention, step (i) is followed by step (ii) described below.

Step (ii), which is a step of constructing, on the basis of the reference β-galactosidase amino acid sequence, the amino acid sequence in which proline is substituted for the amino acid(s) identified in step (i).

(Preparation Method of Modified β-Galactosidase)

A further aspect of the present invention relates to a preparation method of a modified enzyme. In one embodiment of the preparation method of a modified enzyme of the present invention, the modified enzyme that the present inventors succeeded in obtaining is prepared in a genetic engineering technique. In the case of this embodiment, a nucleic acid coding for any one of the amino acid sequences of SEQ ID NOs: 9-15, is prepared (step (I)). Herein, "a nucleic acid coding for a specific amino acid sequence" is a nucleic acid capable of obtaining a polypeptide having the amino acid sequence in the case of being expressed, and as a matter of course of a nucleic acid having a base sequence corresponding to the amino acid sequence, may be a nucleic acid added with an extra sequence (may be a sequence coding for an amino acid sequence or a sequence not coding for an amino acid sequence). Degeneracy of a codon is also considered. "A nucleic acid coding for any one of the amino acid sequences of SEQ ID NOs: 9-15" can be prepared into a state of being isolated by using a standard genetic engineering technique, molecular biological technique, biochemical technique, and the like in reference to sequence information disclosed in the present specification or the appended sequence listing. Herein, all of the amino acid sequences of SEQ ID NOs: 9-15 are obtained by mutation to the amino acid sequence of BgaD-D. Therefore, a nucleic acid (gene) coding for any one of the amino acid sequences of SEQ ID NOs: 9-15 can be obtained also by adding necessary mutation to the gene coding for BgaD-D (SEQ ID NO: 8). A large number of methods for site-directed mutagenesis have been known in the present technical field (for example, see Molecular Cloning, Third Edition, Cold Spring Harbor Laboratory Press, New York), and among those methods, a suitable method can be selected to be used. A method of saturation mutagenesis can be adopted as the method of site-directed mutagenesis. The method of saturation mutagenesis is a "semi-rational, semi-random" technique of assuming a position which relates to a desired function based on a conformation of a protein and introducing amino acid saturation (J. Mol. Biol. 331, 585-592 (2003)). For example, use of a kit such as KOD-Plus-Mutagenesis Kit (TOYOBO CO., LTD.), Quick change (Stratagene Corporation) and Overlap extension PCR (Nucleic Acid Res. 16, 7351-7367 (1988)) makes it possible to introduce position specific amino acid saturation. A Taq polymerase and the like can be used for a DNA polymerase used in PCR. Provided that a DNA polymerase having high precision such as KOD-PLUS- (TOYOBO CO., LTD.) or Pfu turbo (Stratagene Corporation) is preferably used.

In another embodiment of the present invention, a modified enzyme is prepared based on an amino acid sequence that is designed by the designing method of the present invention. In the case of this embodiment, a nucleic acid coding for an amino acid sequence constructed by the designing method of the present invention is prepared in the step (i). For example, based on the amino acid sequence constructed by the designing method of the present invention, necessary mutation (that is, substitution of an amino acid in a specific position in a protein that is an expressed product) is added to a gene coding for a modified enzyme and a nucleic acid (gene) coding for the modified enzyme is obtained.

Following the step (I), the prepared nucleic acid is expressed (step (II)). For example, firstly, an expression vector inserted with the above described nucleic acid is prepared and a host cell is transformed using this constructed vector. The "expression vector" refers to a vector that can introduce a nucleic acid inserted therein into a desired cell (host cell) and is capable of being expressed in the cell. The expression vector generally contains a promoter sequence that is necessary for expression of an inserted nucleic acid, an enhancer sequence that promotes expression, and the like. An expression vector containing a selection marker can also be used. When such an expression vector is used, presence or absence (and its degree) of the expression vector can be confirmed by using a selection marker.

Then, a transformant is cultured under the condition of producing a modified enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 37° C.). A culture time can be set by considering growing characteristics of a transformant to be cultured and production characteristics of a mutant-type enzyme. A pH of a medium is set within the range wherein a transformant grows and an enzyme is produced. The pH of a medium is preferably set at about 6.0 to 9.0 (preferably at around pH 7.0).

Subsequently, the expressed product (modified enzyme) is recovered (step (III)). A culture liquid containing cell bodies after culture may be used as an enzyme solution directly or after undergoing condensation, removal of impurities, or the like, but the expressed product is generally once recovered from the culture liquid or fungas bodies. When the expressed product is a secretion type protein, it can be recovered from the culture liquid, and in other cases, the expressed product can be recovered from cells. In the case of recovering from the culture liquid, for example, an undissolved substance is removed by filtration and centrifugation on a culture supernatant, and then, a purified product of a modified enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of recovering the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a modified enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and recovery of the expressed product (modified enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

Examples

1. Purposes

A β-galactosidase derived from *Bacillus circulans* (BgaD-D) is used for the production of galacto-oligosaccharides using a transglycosylation reaction with lactose as a substrate (Non-Patent Literature 1). Since lactose has an increased solubility in a solution with increasing temperature, it is desirable that the reaction temperature at which the production of galacto-oligosaccharides is carried out is higher. If the heat resistance of the BgaD-D can be improved by enzyme engineering techniques, then an enzymatic reaction at a higher temperature can be carried out in which as a substrate, use is made of a solution of lactose having an increased lactose concentration, and thus an improvement in the productivity of oligosaccharides can be expected. In addition, the production of oligosaccharides at a higher reaction temperature also makes it possible to prevent bacterial contamination. Furthermore, also when an enzyme modification for a different purpose (for example, for a purpose of improving the substrate specificity) has caused an decrease in the stability of the enzyme, a mutation leading to an improvement in its heat resistance would make it possible that an efficient production of oligosaccharides is carried out under the same reaction conditions as before. Thus, improving the heat resistance of BgaD-D by enzyme engineering techniques is very industrially useful. For this reason, the investigation described below was made with the aim of improving the heat resistance of BgaD-D.

2. Methods (1) Analysis of the Steric Structure of BgaD-D

In order to elucidate the steric structure of the BgaD-D, the experimentation described below was carried out. First, a HISTrap HP column (1 mL; GE Healthcare) was used, and purification of BgaD-D was performed using Binding buffer and Elution buffer. The Binding buffer and Elution buffer used in the purification have a composition described below.

Binding buffer: 20 mM sodium phosphate, 0.2 M NaCl, 20 mM Imidazole (pH 7.4).

Elution buffer: 10 mM sodium phosphate, 0.1 M NaCl, 0.25 M Imidazole (pH 7.4).

After the purification was performed as mentioned above, an Amicon Centricon YM-10 (Millipore, Billerica, Mass., USA) was used to carry out dialysis of a sample of the purified BgaD-D enzyme against a buffer of 20 mM Tris-HCl (pH 8.0) to further concentrate the enzyme to 10 mg/ml. The resulting concentrated sample was used to carry out screening experiments under different crystallization conditions. As a result, a hanging-drop vapor-diffusion method using, as a precipitating agent, 0.4 M sodium citrate tribasic dihydrate, 1.0 M sodium acetate trihydrate (pH 4.0), and 25% w/v Polyethylene glycol 3,350 lead to an success in crystals having been yielded near the interface to the heterogeneous solution. A large synchrotron radiation facility Spring 8 was used to collect reflection data from a resulting crystal. Phase determination was performed with a molecular isomorphous replacement method using *BALBES* (Long et al., 2008), and a success in the final molecule construction was achieved using *COOT* (Emsley & Cowtan, 2004) and REFMAC5 (Murshudov et al., 2011), whereby the steric structure of BgaD-D was obtained. In this way, the inventors were successful in the identification of the steric structure of BgaD-D. The data on the steric structure of BgaD-D has been registered at the Protein Data Bank (at the Institute for Protein Research, Osaka University) under Registration NO: 3WQ7 (not available).

(2) Design of Mutation Sites for Heat Resistance and Generation of Mutated Enzymes On the basis of the steric structural information of the BgaD-D, sites to be mutated that were expected to be effective for making the enzyme more heat-resistant were identified. Specifically, a total of nine sites to be mutated were identified that were suitable for reinforcing β-turns by substitution with proline or introducing a disulfide (SS) bond, thereby to generate mutant enzymes. First, in order to reinforce a portion(s) of BgaD-D where its steric structure are less rigid, proline was substituted for K166, D167, G306, G307, E720, and A833. On the basis of a comparison with *Escherichia coli* LacZ, on the other hand, proline was substituted for G101, G102, and G349, for a purpose of reinforcing β-turns. In this case, both G101 and G102 were substituted with proline (thereby to generate a double mutant). In addition, cysteine was substituted for threonines T211 and T315, which are located so near that in the steric structure, cross-linking can be achieved through a disulfide bond between the substituted cysteines.

Primers corresponding to these mutations were prepared, and these mutations (amino acid substitutions) were introduced using a PCR method. Specifically, such a primer was designed, and KOD plus Mutagenesis kit (Toyobo Co., Ltd.) was used to introduce the mutation by an inverse PCR method. A PCR product was subjected to self-ligation, followed by transformation into *Escherichia coli* strain DH5alpha, according to the kit protocol. Plasmid was collected from transformants, and sequenced to verify whether the mutation had been introduced. Furthermore, the plasmid obtained was transformed into *Escherichia coli* strain BL21 (Takara Bio Inc.) or OrigamiB (Merck), and protein expression was carried out using the following protocol.

(Protocol for Protein Expression)

(i) Preculture a transformant (overnight at 37° C.) in 1.5 mL of LB medium (containing ampicillin).

(ii) Add 0.06 mL of the preculture to 3 mL of LB medium (containing ampicillin).

(iii) Culture at 37° C. for 4 hours.

(iv) Transfer the test tube onto ice, and add 0.75 µL of 1 M IPTG to the tube.

(v) Culture at 15° C. for 24 hours.

(vi) Collect cells, and wash with phosphate buffer (pH 7.4).

(vii) Suspend the pellet in 0.25 mL phosphate buffer (pH 7.4).

(viii) Disrupt the cells by sonication (30 seconds, 3 times).

(ix) Collect the supernatant by centrifugation.

Enzyme purification was performed for analysis with a circular dichroism spectropolarimeter. The BgaD-D and its mutated variants were expressed as fusion proteins having a HIS tag attached at the N terminus, and purified using a nickel column. Specifically, a HISTrap HP column (1 ml; GE Healthcare) was used, and purification of an expressed enzyme was performed using the following buffers.

Binding buffer: 20 mM sodium phosphate, 0.2 M NaCl, 20 mM Imidazole (pH 7.4).

Elution buffer: 10 mM sodium phosphate, 0.1 M NaCl, 0.25 M Imidazole (pH 7.4).

The enzyme was bound to the column in Binding buffer, and the column was washed with the same buffer. Then, the bound components were eluted with Elution buffer from the column. The elution sample was subjected to electrophoresis and measurement of hydrolysis activity to verify whether the enzyme had been purified.

(3) Simplified Assessment of Modified Enzymes in Terms of Enzyme Activity

Hydrolysis measurements were carried out with reference to a previous application (WO 2010/140435). As a substrate, use was made of o-Nitrophenyl-β-D-galactopyranoside (ONPG), and the enzyme activity was determined at two temperatures. When lactase was subjected to reaction with ONPG (at a final concentration of 20 mM) at pH 6.0 at a temperature of 40° C. or 60° C., the amount of the enzyme which produced 1 μmol o-Nitrophenyl per minute in an initial reaction phase was defined as one unit (U). An extract from *Escherichia coli* cells expressing a recombinant enzyme was used as a sample (enzyme), and OD420 values after the reaction at 40° C. and 60° C. were determined to calculate activity values of the enzyme.

(4) Assessment of Thermal Denaturation of Single Mutation Variants (Single Mutants)

Wild-type and mutant (mutated BgaD-D) enzymes were expressed, followed by purification with a HISTrap HP column (1 ml). On the basis of the amino acid sequence of BgaD-D, the factor for determination of protein concentrations based on optical density was calculated to be 1.882 OD(280)=1 mg/ml protein, and the protein concentration in a solution of a purified enzyme was determined from its OD280 measurement result. The denaturation temperature was determined using a thermal stability determining program of a circular dichroism spectropolarimeter. By reference to a published article (Yamashiro, K., Yokobori, S. I., Koikeda, S., & Yamagishi, A. (2010). Improvement of *Bacillus circulans* β-amylase activity attained using the ancestral mutation method. Protein Engineering Design and Selection, 23(7), 519-528), measurement conditions for a circular dichroism spectropolarimeter were set as follows:

Instrument: Circular dichroism spectropolarimeter J-820 (Japan Spectroscopic Corporation (JASCO))

Sample concentration: 0.1 mg/ml

Buffer: 20 mM Tris-HCl (pH 8.0)

Measurement wavelength: 222 nm

Temperature increase rate: 1° C./min

Measurement temperature: 45 to 90° C.

(5) Assessment of Thermal Denaturation of Multiple Mutants

Wild-type and multiply mutated variant enzymes were subjected to an assessment of thermal denaturation using the same method and conditions as those described above.

3. Results (1) Simplified Assessment of Modified Enzymes in Terms of Enzyme Activity With wild-type (WT) and nine mutants, their enzyme activity was investigated at 40° C., which is a usual temperature in activity measurement. As a result, a single mutant G306 P was found to exhibit a general decrease in the enzyme activity (FIG. 1(A)). Since it was intended to enhance the heat resistance of the enzyme without changing its properties, it was judged that the introduction of the G306 P mutation, which affected the hydrolysis activity, did not meet its intention.

Subsequently, the ONPG hydrolyzing activity was determined at 40° C. and 60° C. to make a simplified comparison of the thermal stability of the enzymes examined. A dual mutant G101 P/G102 P and a single mutant G306 P were found to have little or no enzyme activity at 60° C., and thus it seemed that the thermal stability of these mutants was reduced due to their mutations (FIG. 1(A)). For all the mutants examined, enzyme activities at 60° C. were compared in terms of relative values to those at 40° C. which were used as reference (activity measurements at 60° C. to those of 40° C.). As a result, seven mutants except the G101 P/G102 P dual mutant and the G306 P single mutant had an activity ratio comparable to that of the wild-type enzyme (FIG. 1(B)). Therefore, these seven mutants were considered to be likely to have an improvement in the heat resistance, and an analysis was carried out with a circular dichroism spectropolarimeter.

(2) Assessment of Thermal Denaturation of Single Mutation Variants (Single Mutants)

With the wild-type enzyme and the above-described seven mutants, their denaturation temperatures were determined using a circular dichroism spectropolarimeter. As results, it was observed that the denaturation temperature was increased by 2.9° C. for a single mutant K166P, by 0.3° C. for a single mutant G307 P, and by 0.4° C. for a single mutant A833 P. For the other mutants, on the other hand, their denaturation temperatures were almost the same as that of the wild-type enzyme (FIG. 2). These observations were based on an assessment from five or more measurements under the same conditions and their accumulated measurement results.

As described above, three promising mutation sites were found for use in the present invention. Therefore, multiple mutants in which two or three of these three mutations were combined were generated to investigate whether such combinations lead to an additive improvement in the heat resistance of the enzyme.

(3) Assessment of Thermal Denaturation of Multiple Mutants

Figure 4:
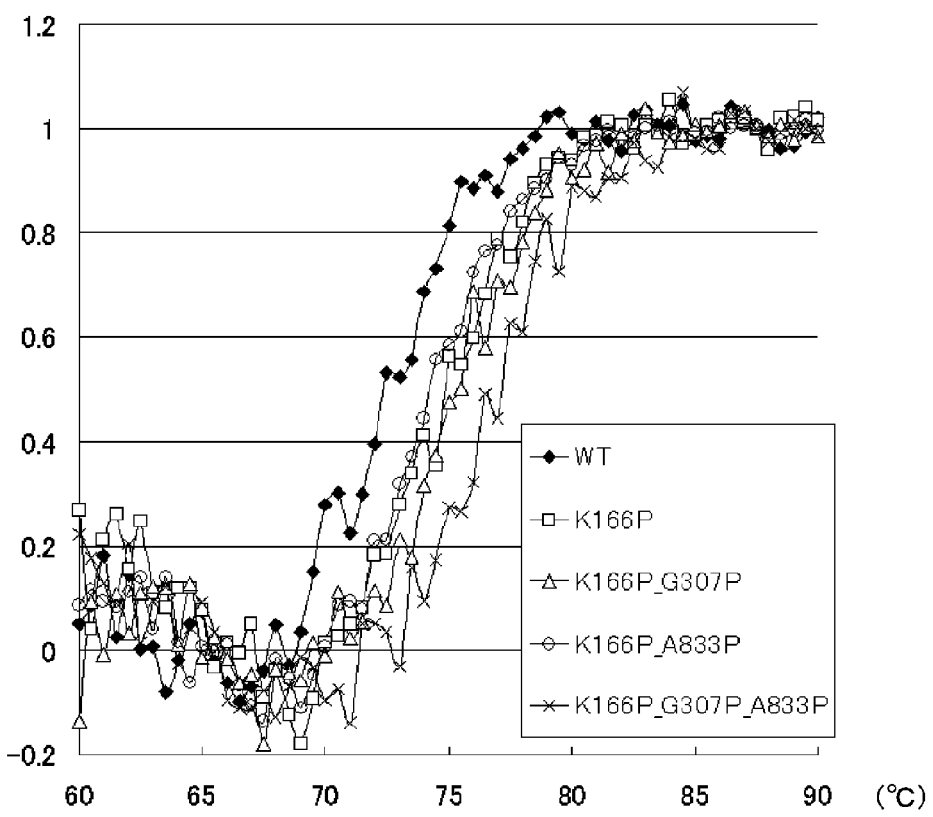
FIG. 4: Changes in CD values (at 222 nm) of wild-type (WT) and K166P-containing variants as a function of temperature.

Wild-type enzyme, three dual mutant enzymes, and one triple mutant enzyme were prepared, and their denaturation temperatures were determined using a circular dichroism spectropolarimeter. As results, it was observed that the denaturation temperature was increased by 3.3° C. for a dual mutant K166P/G307 P, by 1.8° C. for a dual mutant K166P/A833 P, by 0.9° C. for a dual mutant G307 P/A833 P, and by 4.2° C. for the triple mutant K166P/G307 P/A833 P (FIG. 3). Changes in CD values (at 222 nm) obtained with the circular dichroism spectropolarimeter were plotted in a graph to analyze the course of enzyme denaturation. It was found that in comparison to the wild-type enzyme, the mutant enzymes comprising the K166P mutation had a denaturation temperature curve shifted to a higher temperature, and the triple mutant with mutations K166P, G307 P, and A833 P exhibited the greatest shift of the denaturation temperature (FIG. 4). From the results described above, it has turned out that the substitution of proline for K166 and furthermore, a combination of two or more of the modifications is effective for a significant improvement in the heat resistance of the enzyme.

INDUSTRIAL APPLICABILITY

The modified enzyme of the present invention exhibits a heat resistance superior to that of the wild-type enzyme. The modified enzyme can be expected to be employed in the efficient production (synthesis) of oligosaccharides, taking advantage of this characteristic. The present invention can also be employed in the production and processing of pharmaceutical products and supplements for lactose-intolerant patients, production and processing of dairy products (for example, processed milk products such as lactose-reduced milk, powdered milk such as skim milk and nursing powdered milk, yogurts, and others), and production and processing of medical foods.

The present invention should not be limited in any way to the description of the above-described embodiments and examples of the invention. The present invention also includes a variety of modified embodiments within the scope that one skilled in the art could easily arrive without departing from the description of the scope of claims. The contents of articles, published patent applications, patent publications, and others that are expressly provided are incorporated in their entire contents by citation.

---

The invention claimed is:

1. A β-galactosidase comprising an amino acid sequence which is different from a reference β-galactosidase amino acid sequence in that one or more amino acids selected from the group consisting of the following (1) to (3) is/are proline, wherein the reference β-galactosidase amino acid sequence shows a 90% or more identity to the amino acid sequence of SEQ ID NO: 4:

(1) an amino acid corresponding to lysine at position 166 of the amino acid sequence of SEQ ID NO: 4;
(2) an amino acid corresponding to glycine at position 307 of the amino acid sequence of SEQ ID NO: 4; and
(3) an amino acid corresponding to alanine at position 833 of the amino acid sequence of SEQ ID NO: 4.

2. The β-galactosidase according to claim 1, wherein the enzyme exhibits improved heat resistance relative to that of the reference β-galactosidase.

3. The β-galactosidase according to claim 1, wherein the amino acids (1) and (2), the amino acids (1) and (3), or the amino acids (1) to (3) have been subjected to the substitution.

4. The β-galactosidase according to claim 1, wherein the reference β-galactosidase consists of the amino acid sequence of SEQ ID NO: 4.

5. The β-galactosidase according to claim 1, consisting of the amino acid sequence of any one of SEQ ID NOs: 9 to 15.

6. A β-galactosidase comprising an amino acid sequence which is different from a reference β-galactosidase amino acid sequence in that one or more amino acids selected from the group consisting of the following (1) to (3) is/are proline, wherein the reference β-galactosidase amino acid sequence shows a 90% or more identity to the amino acid sequence of any one of SEQ ID NOs: 1 to 3:

(1) an amino acid corresponding to lysine at position 166 of the amino acid sequence of SEQ ID NO: 1, 2, or 3;
(2) an amino acid corresponding to glycine at position 307 of the amino acid sequence of SEQ ID NO: 1, 2, or 3; and
(3) an amino acid corresponding to alanine at position 833 of the amino acid sequence of SEQ ID NO: 1, 2, or 3.

7. A gene encoding the β-galactosidase according to claim 1.

8. A recombinant DNA comprising the gene according to claim 7.

9. A microorganism carrying the recombinant DNA according to claim 8.

10. An enzyme agent comprising the β-galactosidase according to claim 1.

11. A method for producing an oligosaccharide, characterized in that the β-galactosidase according to claim 1 is subjected to a reaction with a disaccharide, oligosaccharide, or polysaccharide having at least one of β-1,3-, β-1,4-, and β-1,6-linkages.

12. A method for designing a β-galactosidase, comprising:
(i) a step of identifying, in a reference β-galactosidase amino acid sequence which shows a 90% or more identity to the amino acid sequence of any one of SEQ ID NOs: 1 to 4, one or more amino acids selected from the group consisting of the following(1) to (3):
(1) an amino acid corresponding to lysine at position 166 of the amino acid sequence of SEQ ID NO: 4;
(2) an amino acid corresponding to glycine at position 307 of the amino acid sequence of SEQ ID NO: 4; and
(3) an amino acid corresponding to alanine at position 833 of the amino acid sequence of SEQ ID NO: 4;

(ii) a step of constructing, on the basis of the reference β-galactosidase amino acid sequence, an amino acid sequence in which proline has been substituted for the amino acid(s) identified in step (i).

13. The designing method according to claim 12, wherein the reference β-galactosidase consists of the amino acid sequence of SEQ ID NO: 4.

14. A method for preparing a β-galactosidase, comprising:
(I) a step of providing a nucleic acid coding the amino acid sequence of any one of SEQ ID NOs: 9 to 15 or the amino acid sequence constructed by the designing method of claim 12;
(II) a step of expressing the nucleic acid; and
(III) a step of collecting the expression product.

* * * * *